US008481295B2

(12) United States Patent
van Leeuwen et al.

(10) Patent No.: US 8,481,295 B2
(45) Date of Patent: Jul. 9, 2013

(54) FUNGI CULTIVATION ON ALCOHOL FERMENTATION STILLAGE FOR USEFUL PRODUCTS AND ENERGY SAVINGS

(75) Inventors: Johannes van Leeuwen, Ames, IA (US); Samir Kumar Khanal, Honolulu, HI (US); Anthony L. Pometto, Anderson, SC (US); Mary L. Rasmussen, Ames, IA (US); Debjani Mitra, Ames, IA (US)

(73) Assignee: Johannes van Leeuwen, Ames, IA (US)

( * ) Notice: Subject to any disclaimer, the term of this patent is extended or adjusted under 35 U.S.C. 154(b) by 399 days.

(21) Appl. No.: 12/657,818

(22) Filed: Jan. 28, 2010

(65) Prior Publication Data
US 2010/0196994 A1 Aug. 5, 2010

Related U.S. Application Data

(63) Continuation-in-part of application No. 11/765,620, filed on Jun. 20, 2007.

(60) Provisional application No. 61/147,944, filed on Jan. 28, 2009, provisional application No. 61/206,535, filed on Jan. 29, 2009.

(51) Int. Cl.
*C12P 1/02* (2006.01)
*C12N 1/14* (2006.01)

(52) U.S. Cl.
USPC ........................................ 435/171; 435/254.1

(58) Field of Classification Search
USPC .................. 435/41, 171, 243, 254, 264, 254.1
See application file for complete search history.

(56) References Cited

U.S. PATENT DOCUMENTS

| | | | | |
|---|---|---|---|---|
| 2,556,084 | A | * | 6/1951 | Hildebrandt et al. ......... 435/165 |
| 3,899,376 | A | | 8/1975 | Azarowicz |
| 3,979,283 | A | | 9/1976 | Prudom |
| 4,056,636 | A | | 11/1977 | Muller |
| 4,081,367 | A | | 3/1978 | Hulls |
| 4,113,612 | A | | 9/1978 | Sekoulov |
| 4,144,132 | A | | 3/1979 | Lines |
| 4,243,685 | A | | 1/1981 | Simon |
| 4,256,573 | A | | 3/1981 | Shimodaira |
| 4,551,250 | A | | 11/1985 | Morper |
| 4,622,982 | A | | 11/1986 | Gaisch |
| 4,627,917 | A | | 12/1986 | Morper |
| 4,800,021 | A | | 1/1989 | Desbos |
| 4,816,158 | A | | 3/1989 | Shimura |
| 5,075,088 | A | | 12/1991 | Lowe |
| 5,296,138 | A | | 3/1994 | Walter |
| 5,354,818 | A | | 10/1994 | Vazza |
| 5,413,713 | A | | 5/1995 | Day |
| 5,418,166 | A | | 5/1995 | Ehlinger |
| 5,449,453 | A | | 9/1995 | Tang |
| 5,525,228 | A | * | 6/1996 | Dague et al. ................. 210/603 |
| 5,567,314 | A | | 10/1996 | Chigusa |
| 5,707,524 | A | | 1/1998 | Potter |
| 5,776,344 | A | | 7/1998 | McCarty |
| 5,811,289 | A | | 9/1998 | Lewandowski |
| 5,879,928 | A | | 3/1999 | Dale |
| 5,981,233 | A | | 11/1999 | Ringpfeil |
| 6,036,854 | A | | 3/2000 | Potter |
| 6,444,204 | B1 | | 9/2002 | Kuznetsov |
| 6,664,100 | B2 | | 12/2003 | Reverso |
| 7,160,714 | B2 | | 1/2007 | Matano |
| 2006/0233864 | A1 | | 10/2006 | Power |
| 2007/0184541 | A1 | * | 8/2007 | Karl et al. ..................... 435/161 |

FOREIGN PATENT DOCUMENTS

| | | |
|---|---|---|
| CN | 1151834 | 6/1997 |
| CN | 1297993 | 6/2001 |
| CN | 1297994 | 6/2001 |
| JP | 01224012 | 9/1989 |
| JP | 07274942 | 10/1995 |
| SU | 1175877 | 8/1985 |

OTHER PUBLICATIONS

"Conversion of Thin Stillage to Methane to Increase the Net Energy Balance of Corn Ethanol", http://www.greencarcongress.com/2008/08/conversion-of-t.html Aug. 5, 2008.
"Reactor Model for Determining KLa", ct-cr4.chem.uva.nl/AirliftExpt/main.html printed Jan. 2, 2008, 5 pages.
"Utilization of Agroindustrial By-Products and Crop Residues by Monogastric Species in Europe", Proceedings of the FAO/ILCA Expert Consultation Mar. 5-9, 1984,15.
American Public Heal th Assoc., et al., "Standard methods for the examination of water and wastewater", 20 ed. Washington DC, USA: APHA/AWWA/WEF 1998.
Antai SP, Crawford DL., "Degradation of softwood, hardwood, and grass lignocelluloses by two *Streptomyces* strains", Appl Environ Microbiol 1981, 42: 378-80.
Association of Official, Analytical Chemists, "Official methods of analysis", 17th ed. Virginia, USA: AOAC International, 2005.
Cheeke, PR, "Applied animal nutrition: Feeds and feed", New Jersey. USA: Pearson Education, Inc. 2005.
Coulibaly, et al., "Utilization of Fungi for biotreatment of raw wastewaters", African J. of Biotechnology, Dec. 2003,2(12): 620-630.
Da Nobega Gaiao, Edvaldo et al., "Digital image-based titrations", Analytica Chimica Acta 2006, 570: 283-290.
Dhaouadi, Hatem et al., "Gas—liquid mass transfer in an airlift reactor-analytical solution and experimental confirmation", Chemical Engineering and Processing, 2001, 40: 129-133.

(Continued)

*Primary Examiner* — Ruth Davis
(74) *Attorney, Agent, or Firm* — Brick Gentry PC; Brian J. Laurenzo; Jessica Susie

(57) ABSTRACT

A method of processing stillage from fermentation derived alcohol is disclosed, including dry-grind ethanol production from corn, by fermentation with filamentous fungi. This produces high-value fungal biomass that can be recovered by screening, is easily dewatered and used as an animal feed, human food or as a source of nutraceuticals. The methodology uses an airlift reactor to enhance the morphology of the fungi for easy harvesting and separation of water for recycling and reuse and to recover added enzymes and mineral acid with the water. The process also separates oil from the stillage. The fungal processing removes organic substances from the water that are otherwise inhibitory to the reuse prospects for the water, i.e. suspended and dissolved organic matter, including glycerol, lactic and acetic acids. The process also separates oil from the stillage by enmeshing the oil in the fungal biomass and can produce more oil through cultivation of oleaginous fungi. This approach generates revenue from low value thin stillage, while substantially reducing stillage processing costs, mainly by averting the need for evaporation of the thin stillage.

35 Claims, 17 Drawing Sheets

OTHER PUBLICATIONS

Dhiraj, A et al., "Solid-state production of phenolic antioxidants from cranberry pomace by *Rhizopus oligosporus*", Food Biotechnol 2002, 16(3):189-210.

Dubois, M. et al., "Colorimetric method for determination of sugars and related substances", Anal Chem 1956,28(3):350-56.

Dunn, L., "Personal communication through Lincolnway Eenergy, LLC", 2008.

Eklund-Jensson et al., "Tempe Fermentation of Whole Grain Barley Increased Human Iron Absorption and InVitro Iron Availability" The Open Nutrition Journal 2008, 2,42-47, Bentham Science Publishers Ltd.

Fu, Chun-Chong et al., "Performance of airlift bioreactors with net draft tube", Enzyme and Microbial Technology 2003, 33: 332-342.

Gate Information Service, Techni, "Anaerobic Methods of Distillery Waste and Wastewater Treatment", Naturgerechte Technologien. Bau-und Wirtschaftsberatung (TBW) GmbH Frankfurt, Germany, Jun. 2000,9 pages.

Gautam, P et al., "Microbial production of extracellular phytase using polystyrene as inert solid support", Bioresour Technol 2002, 83(3): 229-33.

Gavrilescu, M. et al., "Performance of airlift bioreactors in the cultivation of some antibiotic producing microorganisms", Acta Biotechnologica 1998, 18(3): 201-229.

Jasti, N et al., "Converting corn wet-milling effluent into high-value fungal biomass in an attached growth bioreactor", Biotechnol Bioeng 2008, 101 (6):1223-33.

Jasti, N et al., "Fungal treatment of corn processing wastewater in an attached growth system", Water Practice Technol 2006, 1 (3).

Jasti, N et al., "Influence of selected operating parameters on fungal biomass production in corn ethanol wastewater", J Environ Eng 2009.

Jin, B et al., "A bioprocessing mode for fungal biomass protein production and wastewater treatment using an external airlift bioreactor", J Chem Technol Biotechnol 2001,76:1041-48.

Jin, B et al., "A comprehensive pilot plant system for fungal biomass protein production from starch wastewater", Advances in Environmental Research 2002, 6: 179-189.

Jin, B et al., "Characterization and improvement of oxygen transfer in pilot plant external air-lift bioreactor for mycelial biomass production and wastewater treatment", World J Aool Microbiol Biotechnol 2001b, 17:265-72.

Jin, B et al., "Integrated biotechnological fungal biomass protein production and wastewater reclamation, environmental bioengineering", Wang LK, Tay HJ, Tay STL, Hung YT, editors. Handbook of environmental engineering, vol. 11, Totowa, NJ, USA: The Humana Press, Inc. 2009, p. 465.

Jin, B et al., "Mycelial morphology and fungal protein production from starch processing wastewater in submerged cultures of Aspergillus oryzae", Process Biochem 1999, 34{4}:335-40.

Jin, B et al., "Production of fungal protein and glucoamylase by Rhizopus oligosporus from starch processing wastewater", Proc. Biochem 1999,34(1): 59-65.

Jin, B et al., "Screening and selection of microfungi for microbial biomass protein production and water reclamation from starch processing wastewater", J Chern Technol Biotechnol1999, 74:106-10.

Jin, B et al., "The influence of geometry on hydrodynamic and mass transfer characteristics in a new external airlift reactor for the cultivation of filamentous fungi", World J. Microbiol Biotechnol 1999, 15: 73-9.

Jin, B et al., "Utilization of starch processing wastewater for production of microbial biomass protein and fungal amylase by Aspergillus oryzae", Bioresour Technol1998,66:201-6.

Jones, S. T. et al,, "The influence of external airlift loop bioreactor configuration on bioreactor hydrodynamics", American Society of Agriculture and Biological Engineers, Annual Meeting Presentation, Paper No. 077069 Jun. 17-20, 2007.

Kunduru, MR et at., "Continuous ethanol production by Zymomonas mobilis and Saccharomyces cerevisiae in biofilm bioreactors", J. Ind Microbiol1996, 16: 249-56.

Leathers, Timothy, "Bioconversions of Agricultural Residues to Value-Added Coproducts Yeast-Like Fungi", Abstract printed from website, www.ars.usda.gov/research/Qublications/Qublications. htm?Seq No. 115=12735 5 Jan. 24, 2003, 1 page.

Leathers, Timothy, "Bioconversions of maize residues to value-added coproducts using yeast-like fungi", PUBMED printout. Yeast Res., Apr. 2003, 3(2): 133-40.

Lee, Jeewon, "Biological conversion of lignocellulosic biomass to ethanol", Journal of Biotechnology 56 1997, 1-24.

Merchuk, J. C. et al., "Airlift bioreactors: application to wastewater treatment", Dept. of Chemical Engineering Ben-Guriono University of the Negev, Beer-Sheva, Isreal and AqWise—Wise Water Technologies Ltd. P.O.B. 8698, Netanya 42504, Israel.

Nahas, E., "Control of lipase production by *Rhizopus oligosporus* under various growth conditions", J Gen Microbiol1988, 134(1): 227-33.

National Research Center (NRC), "Nutrient requirements of swine", 10th Ed. Washington, DC: National Academies Press 1998.

Nigam, P, "Process selection for protein-enrichment: fermentation of the sugar industry byproducts molasses and sugar beet pulp", Process Biochem 1994, 29(5): 337-42.

Rasmussen, Mary L. et al., "Bioconversion of thin stillage from corn dry-grind ethanol plants into high-value fungal biomas", American Society of Agricultural and Biologicay Engineers. Annual Meeting Presentation. Paper No. 077030 Jun. 17-20, 2007.

Rasmussen, M et al., "Thin stillage treatment from dry-grind ethanol plants with fungi", Minneapolis, MN, USA: American Society of Agricultural and Biological Engineers (ASABE) Annual International Meeting 2007.

Renewable Fuels Association (RFA), "Growing innovation: America's energy future starts at home", 2009 Ethanol Industry outlook. Washington. DC 2009.

Renewable Fuels Association (RFA), "Industry resources: Coproducts", Accessed Oct. 1, 2009 http://www.ethanolrfa.org/industry/resources/coproducts/10/01/2009.

Renewable Fuels Association (RFA), "Resource center: How ethanol is made", Accessed 10101/2009 http://www.ethanolrfa.org/resource/made/ 10101/2009.

Rhodes, RA et al., "Lysine, methionine, and tryptophan content of microorganisms III. Molds.", Appl Environ Microbiol1960, 9(3): 181-84.

Riggles, David, "Acceptance Improves for Large-Scale Anaerobic Digestion", BioCycle Jun. 1998, 51-55.

Ryan, Daniel R. et al., "Fungal bioremediation of phenolic wastewaters in an airlift reactor", Biotechnol. Prog. 2005, 21: 1068-1074.

Sankaran, S et al., "Ozone as a selective disinfectant for nonaseptic fungal cultivation on corn-processing wastewater", Bioresour Technol 2008, 99(17): 8265-73.

Sankaran, S et al., "Use of filamentous fungi for wastewater treatment and production of high value fungal byproducts: A review", Crit Rev Env Sci Biotechnol 2010.

Schaefer, SH et al., "Retooling the ethanol industry: Thermophilic anaerobic digestion of thin stillage for methane production and pollution prevention", Water Environ Res 2008 , 80(2t 101-8.

Singh, S. et al., "Ozone treatment of process water from a dry-mill ethanol plant", Bioresour Technol2007, 99(6): 1801-5.

Sparringa, RA, et al., "Causes of alkalinization in tempe solid substrate fermentation", Enzyme Microb Technol1999, 25: 677-81.

Sutardi, Buckle KA, "Characterization of extra-and intracellular phytases from *Rhizopus oligosporus* used in tempeh production", Int J Food Microbiol 1988,6:(1):67-79.

Tan, SC et al., "The chitosan yield of zygomycetes at their optimum harvesting time", Carbohydr Polym 1996,30(4):239-242.

Van Leeuwen, J (Hans) et al., "Kinetic model for selective cultivation of microfungi in a microscreen process for food processing wastewater treatment and biomass production", Acta Biotechnol2003, 23(2-3): 289-300.

Shrestha, P., Rasmussen, M.L. Nitayavardhana, S. Khanal, S.K. and van Leeuwen, J,(2010) Value-added Processing of Residues from Biofuel Industries. Chapter 17 In: "Biofuel and Bioenergy from Biowastes and Residues" S.K. Khanal T. Zhang, R. Surampalli, R. Tyagi and B. Lamsal editors. American Society of Civil Engineers. 522 pp, ISBN-10: 0784410895.

Varga, Eniko et al., "High solid simultaneous saccharification and fermentation of wet oxidized corn stover to ethanol", Biotechnology and Bioenaineerina 2004,88(5): 567-574.

Walker, GM, "Yeast physiology and biotechnology", Chichester, UK: Wiley & Sons 1998.

Yanai, K et al., "Purification of two chitinases from *Rhizopus oligosporus* and isolation and sequencing of the encoding genes", J Bacteriol 1992, 174(22): 7398-406.

Yesilada, Ozer et al., "Treatment of olive oil mill wastewater with fungi", Tr. J. of Biology 1999, 23: 231-240.

Zhang, ZY et al., "Production of lactic acid from renewal materials by *Rhizopus* fungi", Biochem Eng J 2007,35: 251-63.

Jin, B et al., "Characterization and improvement of oxygen transfer in pilot plant external air-lift bioreactor for mycelial biomass production and wastewater treatment", World J Appl Microbiol Biotechnol 2001b, 17:265-72. (Title correction of previously presented document).

Leathers, Timothy, "Bioconversions of Agricultural Residues to Value-Added Coproducts Yeast-Like Fungi", Abstract printed from website, www.ars.usda.gov/research/publications/publications.htm?Seq No. 115=12735 5 Jan. 24, 2003, 1 page. (Title correction of previously presented document).

* cited by examiner

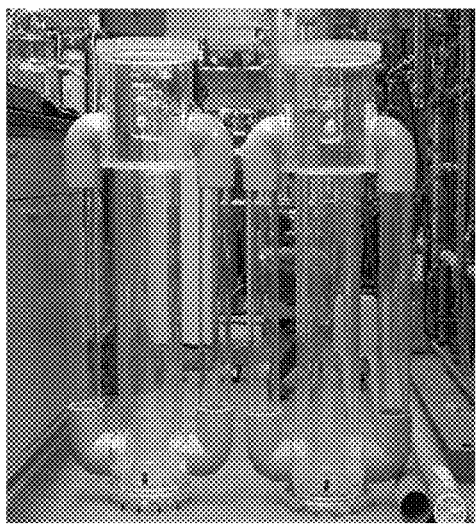
FIG. 4C

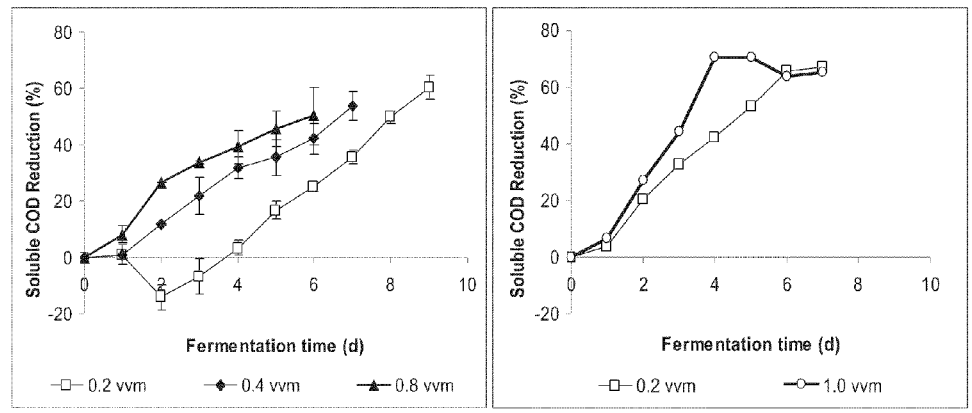
FIG. 8          FIG. 9
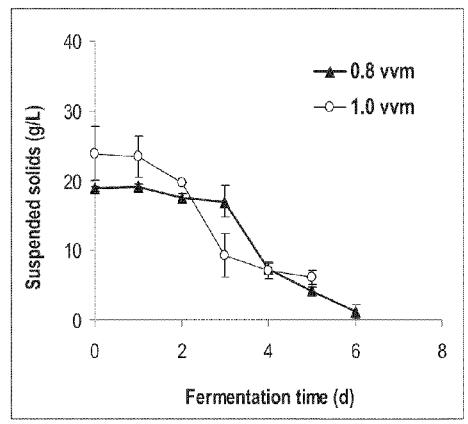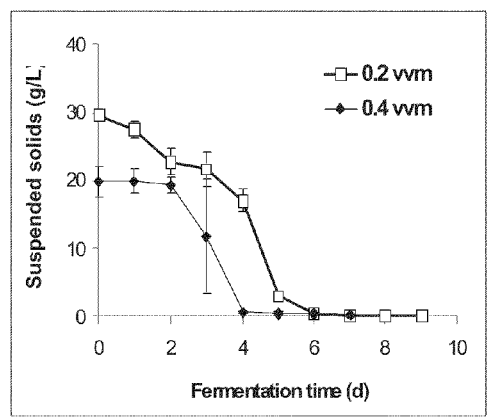
FIG. 10          FIG. 11

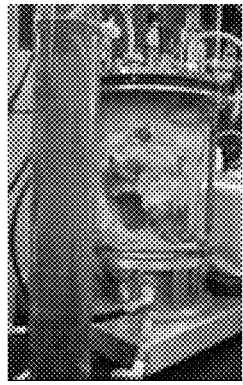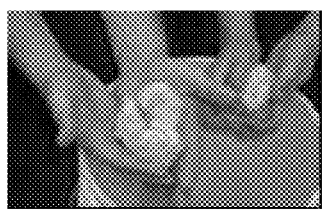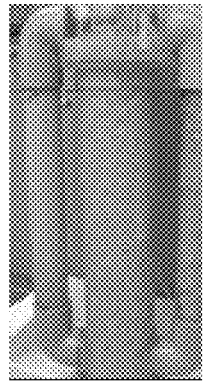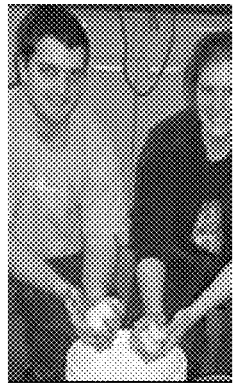
FIG. 21               FIG. 22
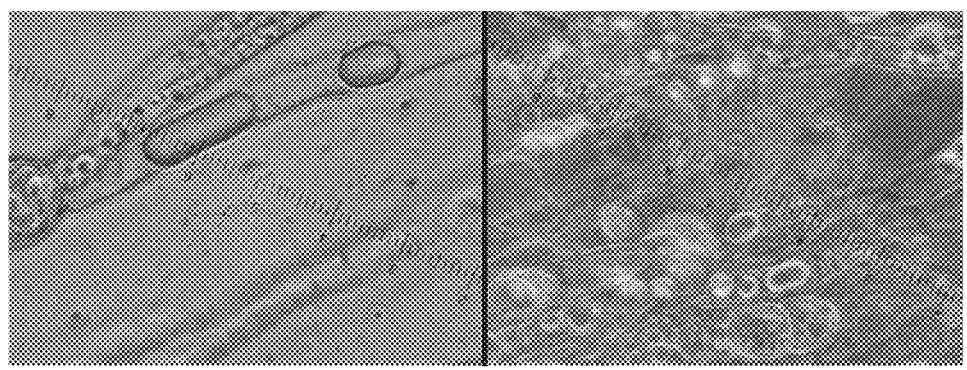
FIG. 23

FUNGI CULTIVATION ON ALCOHOL FERMENTATION STILLAGE FOR USEFUL PRODUCTS AND ENERGY SAVINGS

CROSS-REFERENCE TO RELATED APPLICATIONS

This application is a continuation-in-part of U.S. patent application Ser. No. 11/765,620, filed Jun. 20, 2007. This application also claims priority to U.S. Provisional Patent Application No. 61/147,944, filed Jan. 28, 2009 entitled "Fungi Cultivation on Alcohol Fermentation Stillage for Useful Products and Energy Savings", and U.S. Provisional Patent Application No. 61/206,535, filed Jan. 29, 2009 entitled "Fungi Cultivation on Alcohol Fermentation Stillage for Useful Products and Energy Savings". Each of said applications, all of which, are hereby incorporated by reference in their entirety.

SCOPE OF THE INVENTION

The present invention relates to an improved method of treating of and adding value to co-product streams in the manufacture of ethanol in dry-grind fermentation processes.

BACKGROUND

The production capacity of ethanol from corn in the United States reached 9 billion gallons per year in 2008. The use of ethanol as gasoline additive not only reduces the emission of harmful air pollutants, but also lowers dependence on imported fossil fuels. About six billion gallons of the ethanol produced in 2008 was in dry-grind corn milling plants and this output is set to almost double before 2011 with the capacity currently under construction. Dry-grind corn milling involves milling, cooking, enzyme addition and fermentation by yeasts in water. During fermentation in a corn dry milling facility, only 30-35% of the corn is actually converted to ethanol, about one-third to $CO_2$, and one-third remains as dissolved organics and suspended solids in the (whole) stillage after ethanol removal by distillation in distillation columns. The stillage contains about 89% water.

In a traditional dry-grind ethanol production process more than 75% of the solids in stillage are removed by centrifugation. This solids fraction, known as thick stillage is dried to a product known as distillers dried grains (DDG). Dry-grind corn ethanol plants produced 23.0 million metric tons of distillers grains in 2008, a considerable increase from the 14.6 million metric tons in 2007. The excess centrate, known as thin stillage, is evaporated to produce syrup, which is usually added to the centrifuged solids prior to drying. The dried product from this combination is known as DDG with solubles (DDGS), and is often sold as animal feed. DDGS are low in essential amino acids, particularly lysine (about 0.7%), and methionine (about 0.3%). This limits the use of DDGS in animal feed to part of the ruminant diet mainly, while the demand for feed for hogs and chickens, particularly in the corn belt states, is much larger, DDGS are largely unsuitable as feed for monogastric animals.

The excess water from the centrifuge (centrate), or thin stillage, contains about 3 to 4% suspended solids and 2 to 5% by mass dissolved organic materials. The total content of dissolved and suspended organic materials can be typified by measurement of the oxidizable material and expressed as the amount of oxygen equivalents needed for this oxidation. This is known as the chemical oxidant demand (COD) and the typical value of COD in thin stillage is 100 g/L. This organic material could be available for value-added products.

Disposal of the stream of thin stillage by evaporation, while only recovering a low-value syrup, is a major burden on ethanol plants. Further, the use of syrup in animal nutrition is questionable—with many nutritionists and feeders preferring DDG to DDGS, that is byproduct without solubles. Also, if the distillers grains are not dried, there is no opportunity to combine the syrup with the grains. As a result, many plants end up burning the syrup for some energy recovery or giving it away.

In the ethanol production process, it is a desirable and common practice to recycle thin stillage to the cookers prior to introduction to the fermentors to reduce the need for evaporation to syrup. A maximum of 50% of the thin stillage can be recycled by this mechanism to prevent build-up of inert materials and fermentation byproducts. Fermentation byproducts are essentially waste substances of fermentation and are inhibitory to yeast fermentation. It should be appreciated that most of the organic materials left after fermentation are not amenable to yeast fermentation. The main undesirable components in thin stillage for recycling are the solids and the fermentation byproducts glycerol, lactic acid and acetic acid, which all occur in appreciable concentrations in thin stillage. Recycling of the inert materials and/or fermentation byproducts also results in adding bulk and providing nutrients for unwanted bacterial growths.

An ethanol plant needs about 5 to 6 gallons of water to be added into the fermentation process per gallon of ethanol of produced. Almost half of this is water obtained from the up to 50% recycle of thin stillage. The remainder of the water must be obtained by other means. In other words, additional water must be added to the process. A typical 100 million gallon per year ethanol plant requires 300 million gallons or more of fermentation "make-up water" plus another 120 million gallons per year for other purposes. Most of this water is evaporated as these plants discharge almost no wastewater. As a consequence, at least 500 gallons thin stillage per minute needs to be evaporated on a 100 million gallon/year ethanol plant—adding up to as much as 25 billion gallons per year industry wide. Evaporation is costly and adds about $0.10 per gallon to the cost of producing ethanol (2008 costs), uses non-renewable energy (natural gas usually) and it releases volatile air pollutants. Although heat recovery from evaporation lowers the energy requirements, thin stillage evaporators represent a bottleneck in expanding production on existing ethanol plants. Current plants attempt to lower the evaporation cost through heat recovery from water. Some plants condense the water, but the condensate is rich in volatile organic acids that necessitate additional treatment (such as anaerobic bacterial treatment in a methanator) for organic removal before the water can be reused as process water.

As discussed, in the typical ethanol production process the non-volatile organic material in the thin stillage is concentrated into a low-value syrup. This organic material, along with the volatile organic compounds lost during evaporation, represents a resource that could be converted into more valuable co-products with a higher value. There are other low-value streams generated in other crop-processing industries such as the stillage from fermentation of other grains, sugar cane, agave plants or molasses to ethanol, starch or sugar wastes, stillage from the production of other alcohols and also the whey left-over in soy processing. These streams all represent underutilized resources that could be used in generating more valuable co-products.

Ethanol production is still growing rapidly. As already noted, ethanol is produced mainly by dry-grind corn milling, co-producing considerable amounts of DDG and low-value thin stillage. Profitability in the ethanol industry is threatened by corn prices rising due to increased demand, while DDG may flood the market. In addition, it is to be expected that input energy costs will continue to increase as was demonstrated by the huge spike in oil and natural gas cost in mid-2008. Thus, the industry needs to adapt. The present invention is directed to value adding to an ethanol production process through providing additional co-products, extending marketability, reducing external enzyme needs and saving energy by eliminating the need to evaporate water from thin stillage.

SUMMARY OF THE INVENTION

A method for cultivating fungi is disclosed. The method comprises application of fungi of the phyla Deuteromycota and Zygomycota and the phylum Ascomycota, excluding the order Saccharomycetales, which includes the family Endomycetaceae to which the genus of the imperfect yeast *Geotrichum* belongs, in a fungal bioreactor with stillage left over after distillation of alcohols from a fermented mash of plant material as substrate.

A method of processing stillage from fermentation-derived alcohol is also disclosed, including dry-grind ethanol production from corn, by fermentation with filamentous fungi. This produces high-value fungal biomass that can be recovered by screening, is easily dewatered and used as an animal feed, human food or as a source of nutraceuticals. The methodology uses an airlift reactor to enhance the morphology of the fungi for easy harvesting and separation of water for recycling and reuse and to recover added enzymes and mineral acid with the water. The process also separates oil from the stillage. The fungal processing removes organic substances from the water that are otherwise inhibitory to the reuse prospects for the water, i.e. suspended and dissolved organic matter, including glycerol, lactic and acetic acids. The process also separates oil from the stillage by enmeshing the oil in the fungal biomass and can produce more oil through cultivation of oleaginous fungi. This approach generates revenue from low value thin stillage, while substantially reducing stillage processing costs, mainly by averting the need for evaporation of the thin stillage.

BRIEF DESCRIPTION OF THE DRAWINGS

FIG. 4C illustrates two completed reactors from transparent material, a reactor while in operation, the white balls in the reactor being fungal biomass pellets, as well as an illustration of a pilot-scale reactor built to said design.

FIG. 8 illustrates soluble COD reductions during fungal cultivation of thin stillage in batch stirred bioreactors, 5 L (n=2).

FIG. 4 illustrates soluble COD reductions in 50 L reactor (n=1), with increasing aeration rates of 0.2 to 1.0 vvm.

FIGS. 10 & 11 illustrate suspended solids reductions during fungal cultivation of thin stillage in batch stirred bioreactors (5 L) with increasing aeration rates of 0.2 to 1.0 vvm (n=2).

FIG. 21 illustrates clarified stillage; and biomass in the background.

FIG. 22 illustrates an airlift reactor with external circulation showing fungal growth and product.

FIG. 23 illustrates *Mucor circinelloides* showing oil within the cells in the mycelia; as well as dense growth of these fungi.

DETAILED DESCRIPTION

The present invention is generally directed to an improved method of treating of and adding value to co-product streams in the manufacture of ethanol in dry-grind fermentation processes, and in particular corn fermentation processes. However, it is contemplated that the methodologies and materials employed herein may be applied to alternative crop products without departing from the overall scope of the present invention. For example the methodologies and materials described herein may be used in industry where other harvested plant products are processed and where low-value product streams emerge with high levels of organic concentrations. As a non-limiting example, low-value streams generated in other crop-processing industries may include, but are not limited to the stillage from fermentation of other grains, sugar cane, agave plants or molasses to ethanol, starch or sugar wastes, stillage from the production of other alcohols and also the whey left-over in soy processing. The method described herein provides a low-energy alternative process for using stillage left over from the distillation of fermented corn broth as a substrate for cultivating various phyla of fungi, also known as mo(u)lds, to produce a high-value fungal biomass and reusable process water that may be recovered by simple means, while also avoiding the energy needs for thin stillage evaporation.

Figure 1:
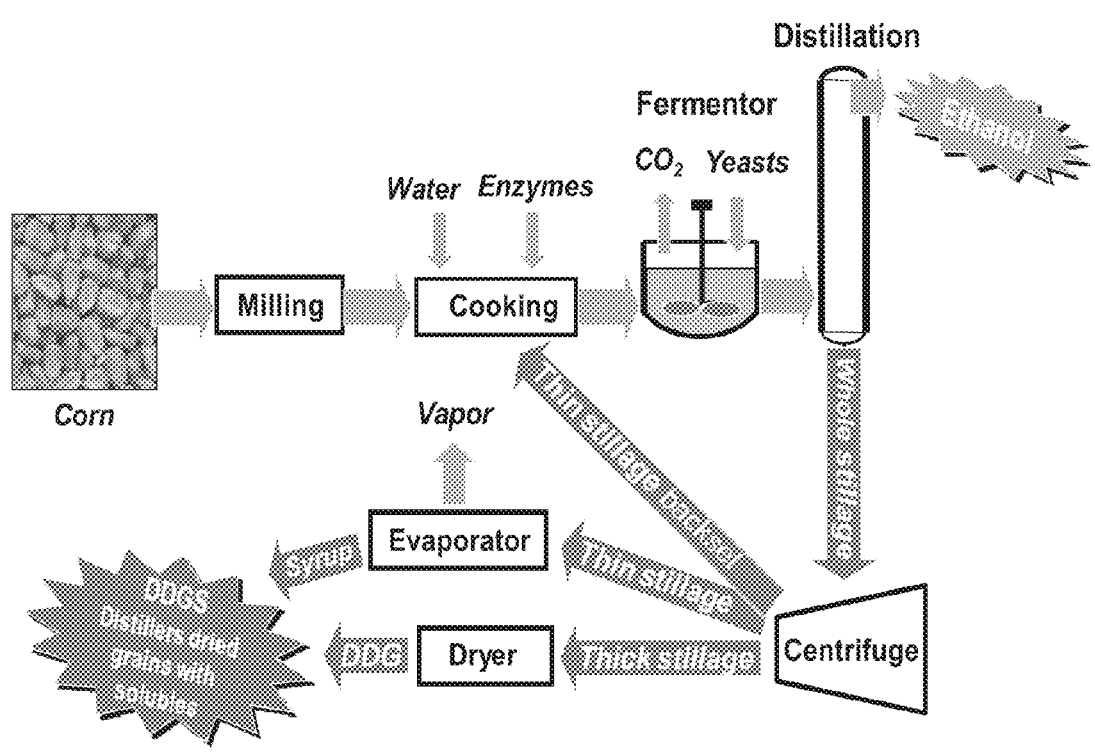
FIG. 1 is a flow chart illustrating a process flow in one or more examples of an embodiment of a dry-grind mill ethanol production process showing the main water streams in fermentation and stillage.

Dry-grind ethanol mills treat their stillage using processing steps as presented in FIG. 1. Part of the thin stillage is evaporated to leave a syrup, which is then blended with distillers dried grains (DDG). The process is energy intensive and, when the vapors are cooled, generates a condensate rich in organic acids that requires additional treatment before it can be used as process water. When this is done, a so-called methanator is used, which is an anaerobic bacterial process, which converts the dissolved organic material to methane and carbon dioxide.

The process described herein is a method for cultivating fungal biomass, or high-value fungal biomass, co-product or low value co-product from an ethanol plant, and more specifically a corn-to-ethanol plant. In the process, whole or thin stillage from dry-grind corn ethanol plants is combined with fungal spores or fungal mycelia at a pH ranging from about 3.5-6.0, and at a temperature ranging from about 20-45° C. in an aerated bioreactor or pond. The combination results in fungal biomass production and purification of water. The fungi in the mixture remove most of the organic matter in the stillage water, including suspended and dissolved solids, glycerol, lactic acid, acetic acid and reducing sugars, enabling direct reuse of the water in the yeast fermentation process. By contrast with the current practice of evaporation of excess stillage, the fungal process saves a substantial part of the energy input required in ethanol production from corn. The fungal biomass is easily harvested as the fungi are inclined to grow in agglomerated pellets, particularly in airlift reactors with internal recycle and more specifically in an airlift reactor with external recycle.

Once produced, the harvested fungal biomass has a high nutrient content that makes it appropriate for use as an animal feed supplement. The fungi is an important source of the essential amino acids lysine and methionine, which are lacking in corn and corn products, and chitosan oligosaccharides, an important growth and immunity enhancer. In this regard, the fungal biomass may be used as a source of valuable nutraceuticals such as chitin, chitosan and glucosamine.

The water from which the fungal biomass is harvested, can be disinfected or pasteurized subsequently to remove microorganisms, but such a treatment may be unnecessary in the reuse process. This water, (which may or may not be treated) in turn, may be recycled for use for a variety of purposes, including for example, corn fermentation with yeasts, fire extinguishing, and floor washing.

The water from which the fungal biomass is harvested may also contain some of the original enzymes, which enzymes can then be reused in the fermentation process through the reintroduction with the water, generating and saving on enzyme addition. Furthermore, since the pH maintained during fungal fermentation is preferably approximately 4-4.5, by reuse of the recycled water in fermentation, the addition of sulfuric acid or any other acid or alkali for pH rectification is not required, thereby averting undesirable sulfate build-up in the water and byproducts.

The fungal cultivation process also separates oils, such as corn oils, contained in the thin stillage, which oils can be recovered as another valuable product. In particular, the oil is concentrated on the fungal biomass. Oleaginous fungi, both filamentous and yeasts, make it possible to produce more oil by the conversion of carbohydrates into oil inside the fungal cells. The oil produced by fungal cells or fungi, termed myco-oil herein, along with, for example, the corn oil collected on the fungal biomass, makes for a useful oil convertible to fuel such as biodiesel or mycofuel.

Figure 2:
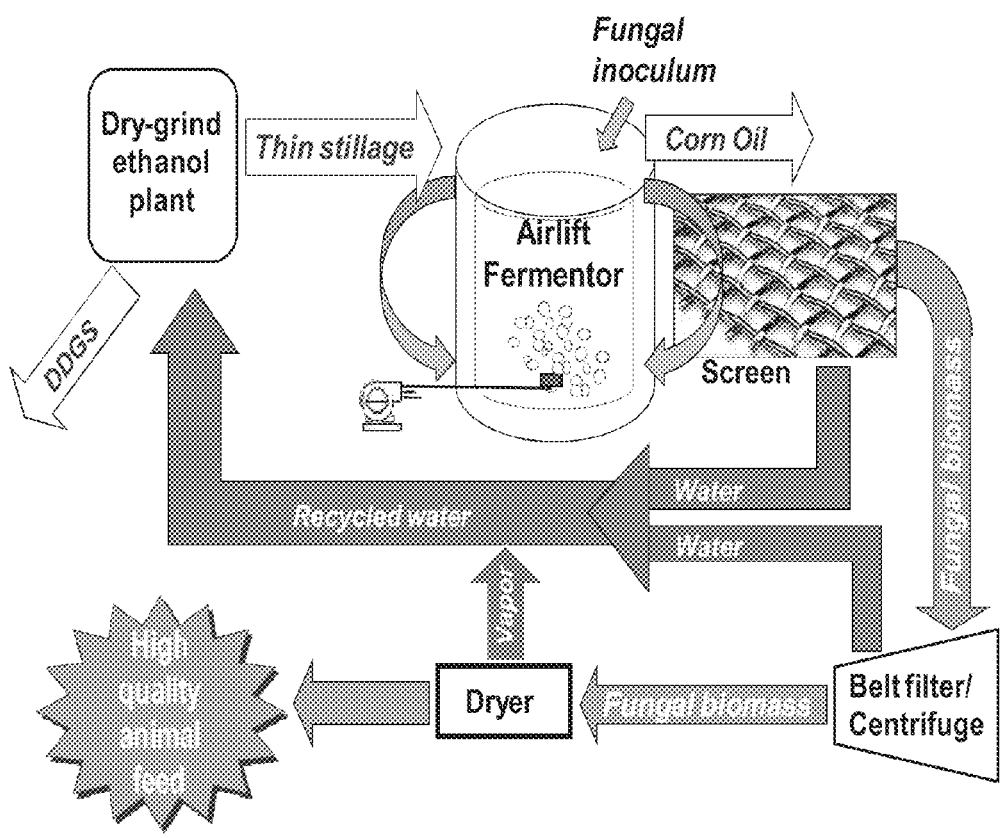
FIG. 2 is a flow chart illustrating a process flow of a dry-grind mill ethanol production process, showing one or more examples of integration of a fungal process for thin stillage treatment and fungal protein recovery, and illustrating one or more processes of fungal production, oil recovery and water reclamation.

The present invention removes dissolved organic material through a fungal cultivation process. In this regard, the thin stillage stream is directed to an aerated fungal reactor (see FIG. 2 and FIG. 3) where most of the dissolved organic materials are converted to valuable fungal biomass or oxidized to carbon dioxide (see FIG. 4). The fungal biomass attaches to the remaining corn solids in the water so that these are readily removed with the fungal biomass. The fungi also remove most of the suspended and dissolved organic material that is undesirable if recycled to fermentation (see FIG. 5). This leaves water that may be reused in corn fermentation (or for various other purposes) following disinfection if required. Unlike traditional ethanol production processes, direct water recycling is possible, thereby saving considerable expenses in evaporation, condensation and further treatment.

The method of the invention first involves obtaining stillage or thin stillage after separating the solids (thick stillage) from the liquid during the ethanol production process.

Analysis of thin stillage has shown that it is rich in a variety of organic substances, nitrogen and phosphate (Table 1). It is rich in organic compounds with a total chemical oxygen demand (COD) of around 100 g/L and a pH of just over 4. It contains enough nutrients such as nitrogen and phosphorus. It is generally free from pathogens and toxicants. These properties make thin stillage an ideal and inexpensive substrate for cultivating fungi with concomitant remediation of process water streams. However, thin stillage alone has a number of undesirables. These undesirables can also be characteristics which do not readily illustrate applicability in a fermentation process, namely there are high concentrations of the undesirable solids, high organics and specifically glycerol, lactic acid and acetic acid. These substances are undesirable in yeast fermentation and limit the recycling of thin stillage under traditional processes. Contrary to current understanding, the molds of the present invention utilize these organic substances, namely a variety of filamentous fungi may be cultivated readily on stillage.

TABLE 1

Characteristics of thin stillage

| Characteristic | Value |
| --- | --- |
| Total solids, g/L | 55--65 |
| Volatile solids, g/L | 50-58 |
| Volatile/total solids | 0.85-0.9 |
| Suspended solids, g/L | 15-30 |
| Volatile suspended solids | 15-30 |
| Total COD, g/L | 80-110 |
| Soluble COD, g/L | 45-55 |
| pH | 4.3-4.6 |
| Volatile fatty acids, g/L | 1-2 |
| Carbohydrates, g/L as glucose* | 12-15 |
| Total Kjeldahl nitrogen, g/L as N* | 5.0-5.5 |
| Total phosphorus, g/L as P* | 1.2-1.4 |
| Glycerol, g/L | 10-15 |
| Lactic acid, g/L | 3-4 |
| Acetic acid, g/L | 1-2 |

*Tested on soluble portion of the sample

As is known, DDG are low in essential amino acids, particularly lysine (about 0.7%) and methionine (0.5%), limiting DDG to use primarily in ruminant nutrition, while many of the ethanol-producing areas have a much larger demand for hog and poultry feed. Lysine and methionine are extremely important for rapid animal growth. By comparison, filamentous fungi, as disclosed herein, contain typically 40% protein including about 3-4% lysine (comparable to soy meal) and 1% methionine (exceeding soy meal). As a result, the fungal biomass may be added to DDG to extend use in swine and poultry rations and to enrich ruminant diets or be used as a separate nutrient supplement in other applications, including the human nutraceuticals market.

The present invention utilizes the ability of fungal cultures to degrade organic compounds present in thin stillage. Tests performed in accordance with the invention show that fungi may be successfully grown in thin stillage with a COD of around 100,000 mg/L having a total solids content of around 6%. Further, the test results demonstrate that the methods of the invention are successful in achieving an organic removal efficiency of up to 90% of the COD, and typically at least 60%, with a fungal yield of about 0.40 g/g $COD_{removed}$. In addition, an almost complete removal of suspended solids, lactic acid and acetic acid is possible. A removal of 70-100% glycerol is also possible.

In order to produce fungal biomass in accordance with one or more preferred embodiments of the invention, the selected microorganism culture has the ability to utilize the waste organic matter and in particular waste organic matter is thin stillage. The microorganisms are also preferably safe (i.e. will not cause health problems to the animal if ingested), able to degrade organic matter from wastewater, have a high protein content (at least 40% by weight), and be easily and reliably maintained in the airlift reactor (FIG. 4).

In one or more examples of embodiments of the invention, the fungal culture is a filamentous fungus of the phyla/divisions Ascomycota, Deuteromycota and Zygomycota and with respect to the phylum Ascomycota, one or more examples or preferred embodiments may exclude the order Saccharomycetales, which includes the family Endomycetaceae to which the genus of the imperfect yeast *Geotrichum* belongs. More preferably, within the Ascomycota the culture may include organisms of the order Eurotiales, specifically the genus *Aspergillus* and the order Saccharomycetales, specifically the genus *Geotrichum* and the order Hypocreales, specifically the genus *Fusarium*. More preferably, within the phylum Zygomycota the culture may include organisms of the order Mucorales with 13 families, 56 genera and 300 species, particularly the family Mucoraceae and of this the genera *Rhizopus, Mucor, Rhizomucor, Absidia* and *Backusella*. The Deuteromycota include the order Moniliales with the family Moniliaceae and the genus *Penicilium*.

A preferred family of fungi for use in the fungal process is Mucoraceae due to the nutritional content of the genera *Rhizopus* and *Mucor*. In this regard, the *Rhizopus* fungi have a high lysine content (3 to 6%), while *Mucor* have a high content of chitosan. *Mucor*, particularly *Mucor circinelloides* may be used in one or more preferable embodiments and is well suited for the synthesis of oil from carbohydrates. Even more preferably, the fungi are *Mucor circinelloides, Mucor indicus (rouxii), Rhizopus microsporus (oligosporus)* and/or mixtures thereof. Such fungal cultures are well known in the art, and are readily obtainable from conventional sources, such as from the American Type Culture Collection and various other sources known in the art. In particular the following accession numbers may be used, *Mucor circinelloides* CBS 277.49 ATCC 1216b; *Rhizopus oligosporus* under ATCC 22959; *Aspergillus oryzae* ATCC 1003. While various organisms and cultures are described herein, the suitable culture may include one or more of the described organisms which may include mixtures thereof suitable for the purposes of the present invention. Likewise, alternative organisms having comparable properties to the listed organisms and cultures may be acceptable for purposes of the present invention.

Prior to incorporation into the stillage, the fungi are "revived" by conventional means using a nutrient broth containing a carbon source, such as dextrose or glucose. In this regard, potato dextrose broth may be used as a preferred carbon source, although other suitable dextrose or glucose sources may be acceptable for the purposes provided.

Figures 4A, 4B:
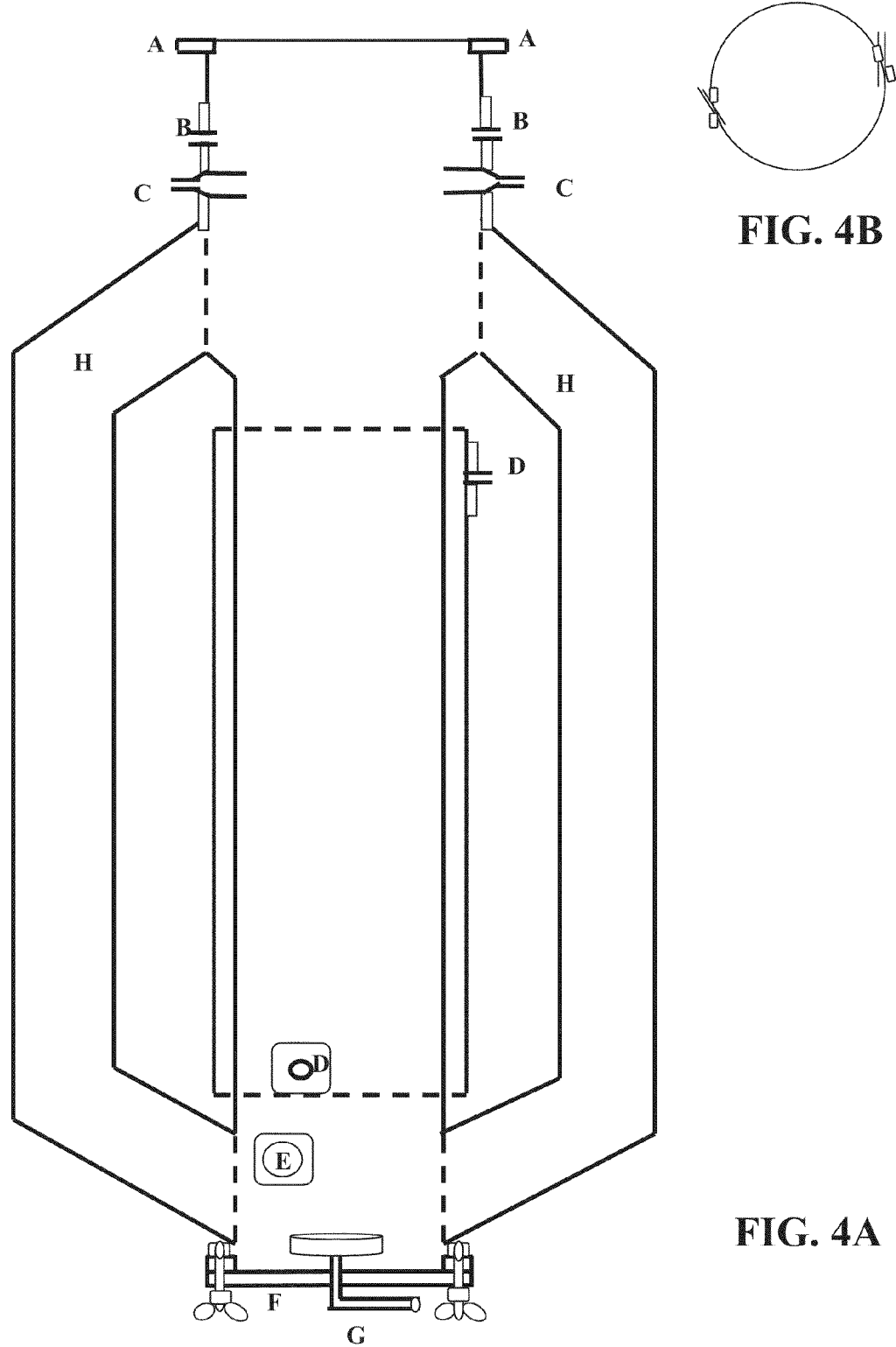
FIG. 4A is a schematic illustration of a fungal bioreactor or airlift fungal cultivation reactor for use with thin stillage fermentation, showing the reactor with external recirculation.
FIG. 4B is cross sectional view of the fungal bioreactor shown in FIG. 4A.
Figure 5:
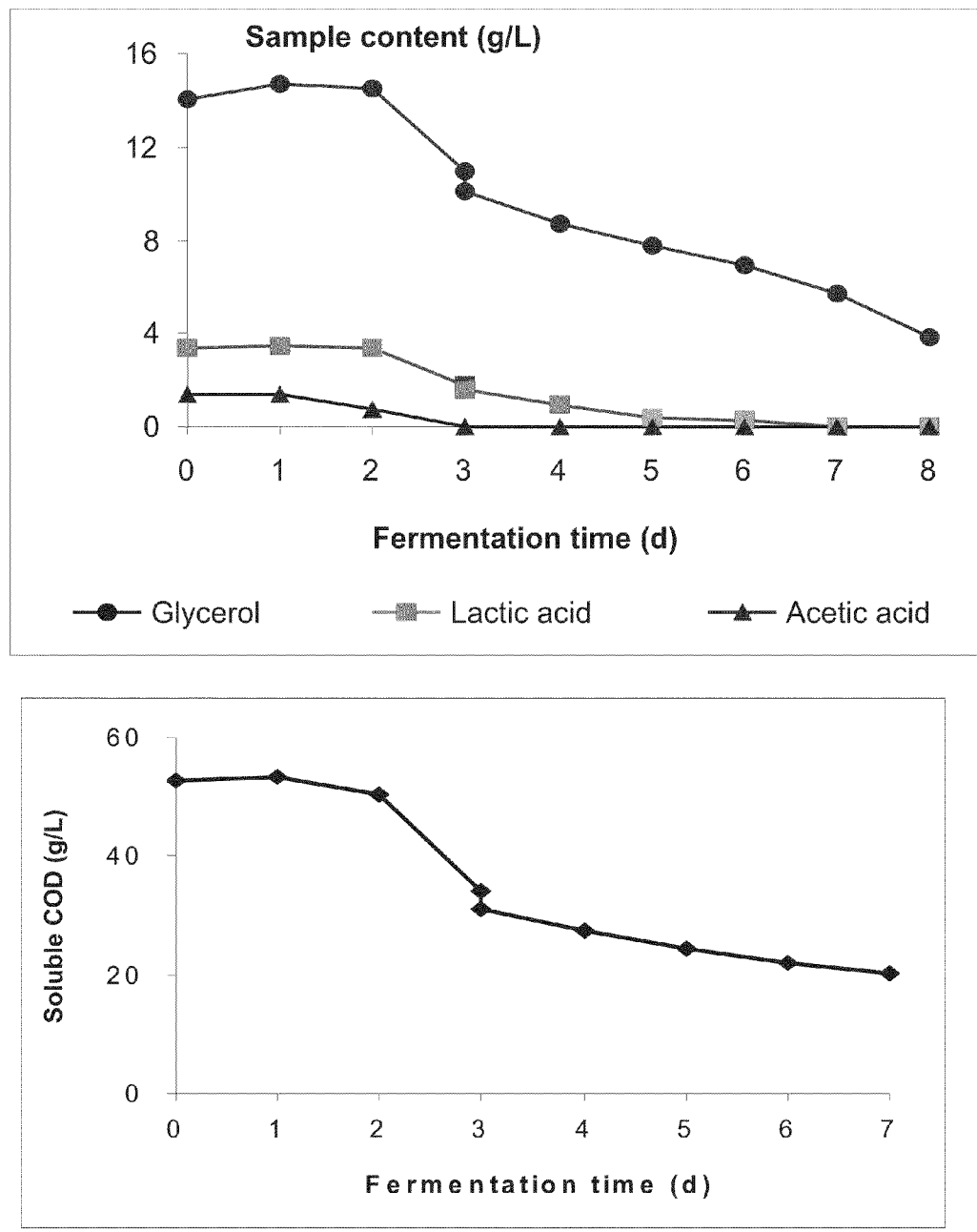
FIG. 5 illustrates a process flow showing removal of impurities, such as glycerol, lactic acid, acetic acid and organic material measured as chemical oxygen demand (COD) from thin stillage by fungal action in one or more examples of the invention.

The process as described according to the invention first involves combining the fungi with stillage. The fungal culture is included or introduced in a fungal bioreactor having stillage left over after distillation of alcohols from a fermented mash of plant materials, which described stillage forms a substrate. The fungi and substrate may be combined in a continuous flow bioreactor or airlift reactor (FIGS. 4A-C) or other appropriate reaction vessel. The continuous flow bioreactor illustrated in FIGS. 4A-C includes a top flange, flushing ports, harvesting ports, heating water ports, a heating jacket, recirculation tubes, access/harvesting ports, porous diffuser(s), and a bottom flange. More specifically, an airlift reactor with recirculation for fungal cultivation is used as described herein. The airlift reactor may be an airlift reactor with internal recirculation. Such airlift reactors are known in the art and include a tank having an internal draft tube concentric to the main cylindrical body of the reactor. Such internal reactors are particularly well suited to large scale assemblies. Alternatively, the airlift reactor may be an airlift reactor or bioreactor having external recirculation. The reactor may be built from any suitable material strong enough to maintain the water pressure resulting from the depth of the device. As illustrated in FIG. 4A, the airlift reactor has a top AA which may be open or enclosed. If the reactor is enclosed, then an air outlet may be provided, and may optionally include a mechanism for air treatment depending upon emission controls. A flange F may attach, such as by bolt or other suitable mechanism to a bottom plate or, in some instances may be grouted into concrete. The bottom flange F preferably has a center inlet G or a plurality of inlets for air. These inlets G may end in fine porous diffusers to introduce air bubbles into the reactor, the aeration rate being a function of the oxygen needs of the system and the fungal growth rate. The reactor further includes water inlets BB which are preferably angled so that the water inlet is almost tangential to the wall of the device which facilitates cleaning of the wall. In the illustrated example (FIG. 4B), one or more water inlets BB may be provided at opposing ends. Recirculation tubes HH are also provided. In operation of the recirculation tubes HH, the air bubbles reduce the density of water with bubbles compared to water without bubbles. The water rises with the bubbles. The bubbles escape at the top and water from the top section, particularly at the wider sides of the reactor, with much fewer bubbles, flows down the recirculation tubes (H and H). The figures generally show the proportion of the diameter of two recirculation tubes to be at half the diameter of the main body as optimal, although variations on such an arrangement are contemplated. Additionally, a plurality of recirculation tubes HH may be provided. Preferably, a different number of recirculation tubes would require that the cross-sectional area of the recirculation tubes be about 50% of the cross-sectional area of the aerated part.

The airlift reactor also includes harvesting ports CC from which contents are gravitated through a screen and the water is partly recycled back to the reactor. Various ports E may be provided for sampling and otherwise introducing measuring devices. In addition, excess water can be recycled for reuse in the main ethanol production plant. If a water jacket is used, additional inlets or outlets DD in the top or bottom of the reactor may be provided.

In a preferred embodiment, heat of the reactor is maintained in a temperature range from 37° C. or 98° F. or lower, although variations from such a temperature may be acceptable for the purposes provided. To this end, a heating jacket or insulation may also be optionally provided on the reactor to retain heat in the reactor. Heating can also be effected by the heat gain in air after pressurization. The fungal cultivation also generates heat and circumstances may arrive where cooling is required, in which case a suitable cooling mechanism may be applied.

In one or more examples of embodiments, Rhizopus or other appropriate molds (filamentous fungi) spores or mycelia are introduced in thin stillage in a 5 L aerated stirred tank reactor with pH, dissolved oxygen and temperature control. More preferably, fungal pellets may be grown, for example, in a shaker then added to autoclaved and centrifuged thin stillage. In this example, about 20-50 mg/L of actively growing fungi may be introduced into the thin stillage in a main reactor. However, autoclaving and/or centrifuging is not required. Thin stillage contains large numbers of micro-particles (corn residues and yeast cells primarily) of 5-100 μm size. Microfungi have a strong affinity to attach to solids causing the micro-particles to act as nuclei for molds to attach to so as to form settleable or easily screenable pellets. These pellets may continue to grow to a size of 3-15 mm by consuming dissolved organics from the aqueous phase of the thin stillage. As a result of this action, the particulate and dissolved organic pollutants are removed from the liquid phase. Thick growths of molds develop rapidly and may be easily separated by screening, settling and/or filtration. In one or more examples of alternative embodiments, the suspended solids in the thin stillage may be removed by settling or high-speed centrifugation before introducing the fungal inoculum, which may facilitate growth of larger mycelial balls.

While large fungal pellets morphology is not essential, separation of pellets is much easier than the separation of smaller fungal particles. The pellets produced in the airlift reactor with external circulation may be separated by settling, dewatered by course screening (¼" openings) and dewatered further by mild pressure, such as on a laboratory scale by hand squeezing, or otherwise by pressure filter.

Figure 3:
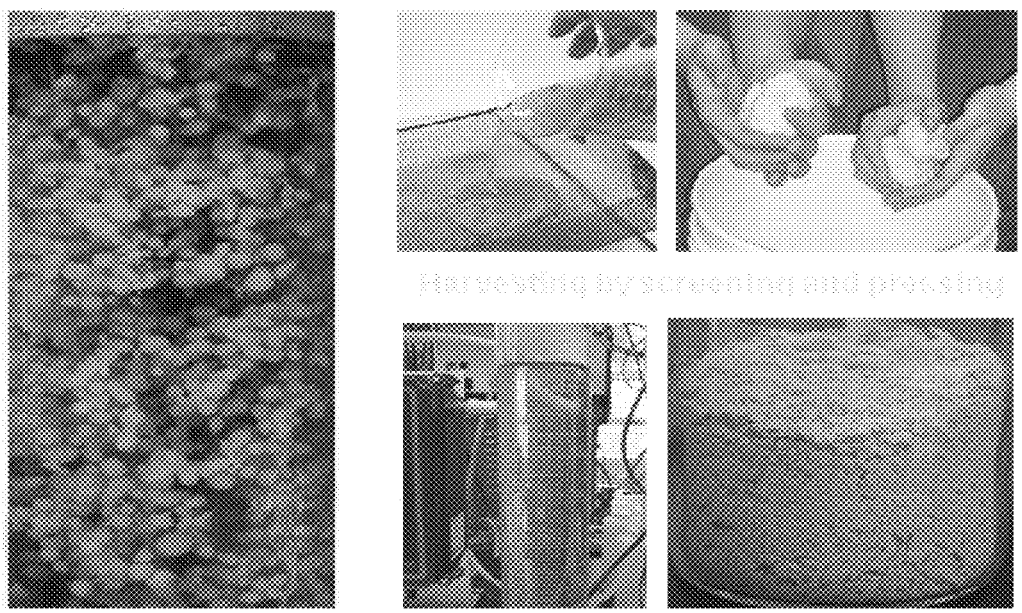
FIG. 3 is an example of a laboratory-scale reactor suitable for operation of the fungal process, showing the reactor in operation including the growth of fungal pellets, separation and harvesting of the fungi by screening, further dewatering of the fungal mass, the recovered water and the freeze-dried product, including fungal biomass growth as readily harvestable pellets or mycelial balls and recovered water.

Growth into larger pellets is further enhanced by higher agitation as caused by aeration and, particularly, by using an airlift reactor with liquid recycling of the reactor content to promote mixing and air release from the suspension (FIG. 3 and FIG. 4). The bioreactor is preferably operated with an air supply rate of greater than 0.1 $L/L_{reactor}$-min, with a preferred air supply rate of about 0.5 $L/L_{reactor}$-min. Reactors with a greater depth will require less aeration in terms of L/L/min or volume/volume/minute (vvm) for the same amount of agitation and oxygen transferred. Shallower reactors may require more aeration, and can ultimately take the form of a pond to simplify construction and lower capital costs.

The processing temperature of the stillage may generally range from 20-45° C. In one or more preferred embodiments, the processing temperature may range from about 30-40° C., with about 37° C. being most preferred. Above ambient temperatures are preferred for purposes of cost and convenience, but not required, as the stillage is already hot after ethanol removal by distillation.

The fungi is preferably inoculated into the stillage at about 1-2% fungal suspension to stillage (0.25% mass), and under conditions favorable to growth of the fungi. In this regard, the pH of the fungi/wastewater mixture is preferably about 3.5-6.0, with about 4.0 being preferred. In one or more examples of embodiments of the invention, the pH is maintained below 4.5. Means for pH control are known in the art and include addition of various industrial acids or bases to the mixture, such as, but not limited to sulfuric acid, hydrochloric acid or phosphoric acid, or lime, and soda. Such pH-controlling agents are preferably compatible with the other ingredients. In one example, the pH controlling agent is a mineral acid which may acidify the mixture to, or near a pH4. While specific pH control examples are provided, pH control may be unnecessary as described herein.

The reactor may be operated at a hydraulic retention time (HRT) of from about 24-160 hours, and a solid retention time (SRT) of from about 12-48 hours. In one or more examples, a shorter fungal retention time than HRT is employed to ensure that the biomass concentration is kept low enough for rapid fungal growth, easy settling/screening/flotation and well clarified effluent. While the reactor may be operated at SRTs of more than 2 days, as a practical matter, SRTs of greater than 2 days may result in impracticably high fungal biomass concentrations, which could complicate aeration and separation and increase the treatment costs without a significant improvement in the effluent quality. The HRT may be determined by the time required to satisfy the oxygen demand and may relate to reactor design to increase the rate of oxygen transfer.

Preliminary test results indicate an organic removal efficiency of over 60% using the methods described above. The fungi grew to a density of around 15 g/L and the normally opaque yellowish color of the thin stillage disappeared within a day, resulting in a clear effluent. As much as 80,000 mg/L of the COD was removed during fungal fermentation by Rhizopus spp., thereby forming fungal pellets of mycelia growing in flocs or pellets that are easily separated by screening.

The fungal biomass, along with corn solids, may be easily separated from the water by screening, settling, or dissolved air flotation. The filamentous fungi assimilate the organic compounds in the wastewater to produce a high quality proteinaceous fungal biomass. This high protein biomass may, in turn, be incorporated into animal feed supplements and pet food, or blended with DDG to improve flavor and feed nutrient value. The enmeshment of the solid particles in the stillage by the fungal mycelia leads to 99% or more removal of suspended solids. This makes for very clear water, important for recycling to reduce or avoid the build up the inert solids in the yeast fermentation process and also recovers this part of the material as animal feed.

The water separated from the fungal biomass may be recycled for various purposes, such as, for example, ethanol fermentation, fire extinguishing, and floor washing. While specific examples of water usage are provided, any suitable use of the reclaimed or recycled water may be acceptable for the purposes provided. Disinfection of the water may or may not be required, and in one or more examples is not required if the water is recycled to a fermentation process involving cooking of, for example the corn mash. In other words, the water is of such high quality that it makes direct recycling of the water into the process possible.

As is known, each dry-grind mill ethanol plant expends millions of dollars per year on enzymes to facilitate the ethanol production process. In one or more examples of the fungal process the particular organism used for the process may also produce a useful enzyme. For instance, Rhizopus sp. are also known to produce α-amylase (Jin et al. 1998) and possibly glucoamylase. In the process according to the invention, the enzymes are retained and preserved in the water without further treatment that may lead to denaturization of the enzymes. Indications from the research are that the amylolytic activity levels in the water after fungal treatment are preferably at levels of 25% of that required for corn processing. Further, recycling enzymes with the recovered water approximately leads to substantial savings—valued at about 1 c/gallon of ethanol produced. The value of enzymes depends on the excess production level available for recycling and may amount to savings of millions of dollars per year.

The fungal process is preferably operated in a pH range for optimum viability of the organism, and is more preferably operated in a pH range from pH 4 to 4.5. The water from this process is therefore acidic and at the same pH as required in the yeast fermentation. Direct recycling introduces water at an appropriate acidity for fungal activity, ultimately generating cost savings, by not having to add acid when water is obtained from a different source, or water recovered by evaporation is used. Further, sulfuric acid, which is most commonly used as a low cost acid, adds to the sulfate content of animal feed produced as a co-product of the ethanol production process, and is detrimental to animal health as it leads to hydrogen sulfide formation during the anaerobic fermentation of feed in the digestive system and belching of malodorous gases. By introduction of the reclaimed water at the appropriate acidity, such harmful addition of sulfate content can be avoided or otherwise reduced.

In addition to the foregoing, the thin stillage contains oil, namely corn oil, which is usually not easy to separate and it is not removed during conventional centrifugation. In a typical ethanol production process, the thin stillage requires additional treatment and separate centrifugation to recover oil from thin stillage. By comparison, fungal cultivation according to one or more examples of the fungal process removes certain substances and particles to which the oil is bound so that the oil is released and the removal of certain inhibitory compounds to the agglomeration of colloidal oil is removed by the fungal cultivation. This makes it possible to either remove the oil by flotation in the top of the fungal reactor or to capture the corn oil by enmeshment and/or adsorption in the fungal biomass.

In one or more examples, more oil, myco-oil, can be produced by using an oleaginous fungus such as *Mucor circinelloides* or a yeast such as the basidiomycete *Cryptococcus curvatus*. It is noted that the foregoing organisms are provided for purposes of example, and other organisms having similar properties or accomplishing the same result may be acceptable for the purposes provided.

EXAMPLES

The following Examples are set forth so as to provide those of ordinary skill in the art with a complete disclosure and description of the methods claimed herein, their performance and evaluation and are intended to be purely exemplary of the invention and are not intended to limit the scope of what is regarded as the invention. For example, they are presented with the understanding that various formulation modifications as well as reactor modifications may be made and still be within the spirit of the invention. Efforts have been made to ensure accuracy with respect to numbers (e.g., amounts, temperature, etc.) but some errors and deviations should be taken into account.

Example 1

Water Reclamation and Fungal Biomass from Corn Ethanol Stillage

1. Introduction

Dry-grind corn ethanol plants, the backbone of a rapidly expanding biofuel industry, generate copious amounts of stillage, the leftovers from fermentation followed by distillation. Most conventional dry-grind corn ethanol plants use on average 3.5 gal of fresh water [1] and generate 5-6 gal stillage per gal ethanol after distillation, of which up to half is recycled directly as backset [2]. The ethanol-to-stillage ratio in the beer from a finished fermentation is limited by ethanol toxicity to the yeast. Most thin stillage is currently concentrated by flash evaporation—an energy-intensive process—blended with distillers grains, and dried to produce distillers dried grains with solubles (DDGS). Thin stillage is generated in pasteurized condition and is rich in nutrients, with a chemical oxygen demand (COD) up to 100 g/L. The initial pH of 4 and high organic content make it an ideal feedstock for fungal cultivation. This research cultivated the food-grade fungus *Rhizopus microsporus* var. *oligosporus* on thin stillage from a local dry-grind corn ethanol plant.

Based on the utility of the fungi and the readily available low-cost substrate, bench- (5 L) and pilot-scale (50 L) experiments were conducted to evaluate fungal treatment of thin stillage for fungal biomass production and organics removal to obtain recyclable effluent for in-plant use. Aeration rates in stirred bioreactors were varied from 0.2 to 1.0 L air/L working volume/min (vvm). Feed stillage and bioreactor samples were analyzed to determine the removal of total and soluble COD (TCOD, SCOD), total and volatile suspended solids (TSS, VSS), glycerol, and lactic and acetic acids, critical for recycling the effluent as process water. Fungal biomass production was quantified, and samples were analyzed for protein and amino acid contents.

2. Materials and Methods 2.1. Thin Stillage

Thin stillage samples were obtained from Lincolnway Energy (Nevada, Iowa, USA), a dry-grind corn ethanol plant. Samples were collected in sterile 10- and 20-L carboys and stored at 4° C. prior to use. The pH of fresh thin stillage was acidic (pH 3.8 to 4.7), and the COD averaged 90 g/L, of which 55 g COD/L was dissolved solids. The total and reducing sugar contents averaged 17 and 6 g/L, respectively. Suspended solids were 20-30 g/L, and the total nitrogen content was 6 g/L. Thin stillage suspended solids settled during storage at 4° C. Supernatant from settled thin stillage (0.2 g/L suspended solids) was used as substrate for preparation of fungal mycelia inoculum and to determine the effect of thin stillage particles on fungal growth and morphology.

2.2. Fungal Culture

Freeze-dried culture of the fungus R. oligosporus was obtained from the American Type Culture Collection (ATCC 22959, Rockville, Md., USA). The culture was revived in yeast mold (YM) broth (Difco Laboratories, Sparks, Md., USA) at 25° C. Plates of potato dextrose agar (Difco Lab) were inoculated with the revived culture and incubated at 25° C. for 5-7 d. Fungal spores were harvested from the plates using sterile deionized water containing 0.1% (w/v) peptone and 0.2% (v/v) Tween 80 (Fisher Scientific, Fair Lawn, N.J., USA). Glycerin (20% [v/v]) was added to the spore suspension prior to ultra-low freezer (−75° C.) storage in sterile 2-ml cryovials. The harvested spore count of $5 \times 10^6$ spores per ml was determined by haemocytometer. Mycelia inoculum was prepared by heat sterilization (121° C. for 20 min) of YM broth or settled thin-stillage supernatant (1 L), inoculation with 1 vial (2 ml) of spore suspension, and incubation at 150 rpm shaking and 37° C. for 3 d (FIG. 1).

2.3. Bioreactor Set-Up and Operation

Batch fungal cultivations on thin stillage were performed in bench-top stirred bioreactors with 5-L working volumes. Bench-top bioreactors were sterilized with water by autoclaving for 45 min at 121° C., drained, and filled with thin stillage aseptically using a peristaltic pump. Culture conditions were chosen based on previous fungal research treating corn ethanol wet-milling wastewater [3]. Once culture conditions stabilized at pH 4, 250 rpm agitation, 37° C., and the filter-sterilized aeration rate chosen for the experiment, the dissolved oxygen (DO) probe was calibrated to 100%. The thin stillage was inoculated with fungal spore suspension ($1 \times 10^7$ spores). The pH was controlled using a pH probe, acid pump, and hydrochloric acid (3 N). An external water jacket maintained the temperature at 37° C. Aeration rates were increased from 0.2 to 1.0 L air/L thin stillage/min (vvm) over successive experiments. Evaporative losses were quantified on a daily basis to compensate for evaporation in sample analyses calculations.

Batch stirred fungal experiments were scaled up to 50-L working volumes. These experiments were operated with similar culture conditions. The bioreactor was steam sterilized, filled aseptically with thin stillage, and inoculated with fungal mycelia (2% [v/v]).

2.4. Sample Analyses

Feed thin stillage and/or daily bioreactor samples were analyzed for TCOD, SCOD, TSS, VSS, nitrogen content, total and reducing sugars, lactic and acetic acids, and glycerol. The COD and suspended solids analyses were performed as described in Standard Methods [33]. The nitrogen content of fresh thin stillage was determined according to the Dumas method [34]. Reducing and total sugars in the thin stillage were measured by using the Somogyi-Nelson carbohydrate assay [4] and the phenol-sulfuric method [5], respectively.

The organic acid and glycerol contents were determined with a Waters high pressure liquid chromatograph (Millipore Corporation, Milford, Mass., USA). The system was equipped with a Waters Model 401 refractive index detector, column heater, autosampler, and computer controller [6]. The sample components were separated on a Bio-Rad Aminex HPX-8711 column (300×7.8 mm) (Bio-Rad Chemical Division, Richmond, Calif., USA) using 0.012 N sulfuric acid mobile phase at 0.8 ml/min, an injection volume of 20 µl, and a column temperature of 65° C.

2.5. Effluent and Biomass Collection

Fungal process effluent was pumped from the bioreactors through the effluent port. Fungal biomass was collected from the bioreactor vessel wall, agitator blades, and probes/ports. Suspended biomass was recovered from the effluent by centrifuging for 20 min at 7,277×g and decanting the supernatant. Attached and suspended biomass was freeze-dried to quantify fungal biomass production and to avoid the potential for heat-drying effects on feed quality for research purposes.

3. Results and Discussion

3.1. Visual Observations

Fungal growth and morphology in 5-L experiments depended on the aeration rate and initial suspended solids concentration. With 0.2-vvm aeration, suspended fungal growth was visible within 4 d of spore inoculation. Accumulation of mycelia was observed on day 4 between the pH and DO probes and the vessel wall. The fungus continued to agglomerate and grow, with considerable clarification of the liquid on day 5. By day 8, the vessel was filled with fungal biomass. Increased aeration of 0.4 vvm triggered biomass agglomeration and liquid clarification on day 4, a day earlier than observed with 0.2-vvm aeration. The fungal mycelia transitioned from suspended growth to attachment on the agitator blades and between the probes and vessel wall. Liquid collected from the effluent port was well-clarified with a yellow tint.

Figure 6:
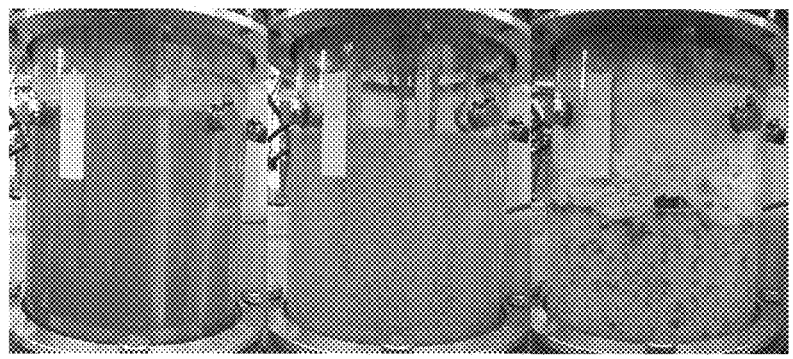
FIG. 6 illustrates fungal cultivation of settled thin stillage supernatant (5 L) in a batch stirred reactor with 0.8 L L$^{-1}$ min$^{-1}$ aeration from (left) spore inoculation (day 0) to day 1 and day 3 (right).

Higher aeration rates of 0.8 and 1.0 vvm promoted a different fungal morphology; fungal mycelia became filamentous flocs on day 4, and some mycelia remained in suspension throughout the 5-L experiments (FIG. 6).

A bench-scale experiment with settled thin-stillage supernatant, 0.1 g/L suspended solids, as compared to 20-30 g/L in thin stillage, was performed to determine the effects of thin stillage particles on fungal cultivation. The liquid began to clarify by day 3. In 50-L experiments, most fungal mycelia and suspended solids remained in suspension. Solids also accumulated above the liquid level on the vessel wall with both 0.2- and 1.0-vvm aeration rates.

Figure 7:
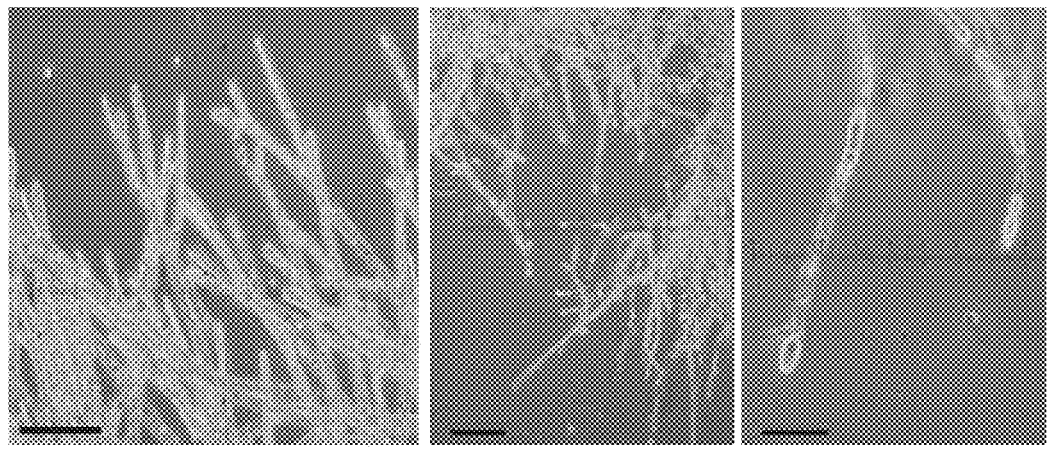
FIG. 7 illustrates microscopic observations of fungal mycelia and sporangiospores grown in settled thin-stillage supernatant on day 1 (left photo) and day 4 (middle and right photo).

The bioreactor was filled with small fungal pellets within 2 days of spore inoculation. The pellets were smaller and more compact, or less filamentous, than fungal flocs formed in the presence of thin stillage particles with the same aeration rate. Fungal mycelia and sporangiospores were observed under the microscope on days 1 and 4, respectively (FIG. 7).

3.2. Organics (COD) Removal

The total and soluble organic content of fresh thin stillage batches, as measured by COD, ranged from 81-98 g TCOD/L and 49-60 g SCOD/L, respectively. Reductions in SCOD tended to improve with increasing aeration rates up to 0.8 vvm in bench-top stirred bioreactors (FIG. 8). The Soluble COD (SCOD) was reduced by 17, 36, and 46% in 5 days with aeration rates of 0.2, 0.4, and 0.8 vvm, respectively. Increasing the aeration rate to 1.0 vvm had a slightly lower SCOD removal in 5 days (42%) than obtained with 0.8 vvm (46%) (data not shown). This outcome may be attributed to the concentrating effect of rapid reduction in liquid volume with 1.0-vvm aeration, due to evaporation and suspended solids accumulating on the vessel wall. The DO level with 0.8-vvm aeration, the optimal rate for SCOD reduction in 5-L bioreactors, dropped rapidly from 100 to 75% of saturation in 1 day and to 3% in 2 days (FIG. 9). The DO averaged 4% from day 2 to day 5.

The initial SCOD of settled thin-stillage supernatant (57 g/L) was within the range of SCOD values for fresh thin stillage with suspended solids as expected. The SCOD in the soluble thin stillage fraction was reduced by 41% in 5 days with 0.8-vvm aeration. The higher reduction (46%) with thin stillage suspended solids may indicate that the particles provided a nutrient that enhanced fungal growth. It may also be a result of the different fungal morphologies, filamentous flocs versus compact pellets, observed with and without thin stillage particles, respectively.

The scaled-up batch fungal bioreactor (50 L) demonstrated a more rapid reduction in SCOD (FIG. 9). The SCOD decreased by 53% in 5 days with 0.2-vvm aeration and by 71% in 4 days with 1.0-vvm aeration; corresponding results for the bench-top experiments were 17 and 39%, respectively. Improved SCOD removals were expected due to more rapid start-up from mycelia inoculum, better oxygen transfer, and less wall effect in the larger bioreactor. The fermentation broth was dense with fungal growth by day 4 with 1.0-vvm aeration. The decrease in SCOD reduction after day 5 may be the result of fungal cell lysis. DO levels during the 50-L fungal cultivation with 1.0-vvm aeration dropped from 100% to 5% of saturation in 1 day. The DO remained low, averaging only 1%, from day 1 to the end of the experiment.

The removal of TCOD was less straight-forward; it depended on the harvesting method, such as settling, centrifugation, or filtration, and the amounts of suspended solids removed by attachment to the fungal biomass. In the 0.2- and 0.4-vvm aeration bench-top experiments, the effluent was well-clarified with almost no suspended solids. The TCOD reductions for the 0.2-vvm aeration effluent reached 55 and 79% in 5 and 9 days, respectively. For 0.4-vvm aeration effluent, TCOD reduction was slightly higher (56% in 5 d). In bench-top experiments with 0.8- and 1.0-vvm aeration and the suspended mycelia separated from the effluent, the TCOD decreased by 58 and 63% in 5 d, respectively. Most of the thin stillage suspended solids and mycelia remained in solution during the 50-L fungal cultivations. Effective separation of these suspended solids from the 5-day effluent would result in TCOD removals of 75 and 84% for 0.2- and 1.0-vvm aeration rates, respectively.

3.3. Suspended Solids Removal

The initial suspended solids were from 20 and 30 g/L in fresh thin stillage batches. Total and volatile suspended solids contents were similar in all experimental samples, indicating low levels of fixed, inorganic suspended solids. Reductions in suspended solids in daily bioreactor samples differed based on the aeration rate (FIG. 10). Gradual removal of suspended solids was observed with 0.2-vvm aeration from day 0 through day 4 (up to 39%), in part due to accumulation on the bioreactor wall above the liquid level and between the probes and vessel wall. The suspended solids concentration decreased rapidly after day 4 reaching 89 and 99% removals by days 5 and 6, respectively; this coincided with the liquid clarification observed on day 5 (TCOD and SCOD became equal). Thin stillage particles were removed by attachment to mycelia and by biological mineralization.

Liquid collected through the effluent port was well-clarified, as low as 20 mg/L suspended solids, with a yellow tint. Solids separation before returning the water to the corn fermentation process is very important to avoid the build-up of non-biodegradable substances. The fungal process effluent could potentially be recycled with minimal further treatment. An increased aeration rate of 0.4 vvm resulted in more rapid clarification of the bioreactor samples on days 3 and 4 (FIG. 11). The average removals with 0.4-vvm aeration were 45 and 97% in 3 and 4 days, respectively.

Suspended solids contents in bioreactor samples with 0.8- and 1.0-vvm aeration were higher than observed with lower aeration rates because fungal mycelia remained in suspension throughout the experiment. Clarification of the bioreactor samples, due to thin stillage solids removal by degradation and attachment, occurred on day 4 with aeration of 0.8 vvm and day 3 with 1.0 vvm, as compared to days 5 and 4 with 0.2 and 0.4 vvm, respectively.

3.4. Organic Acids and Glycerol Removal

Figure 12:
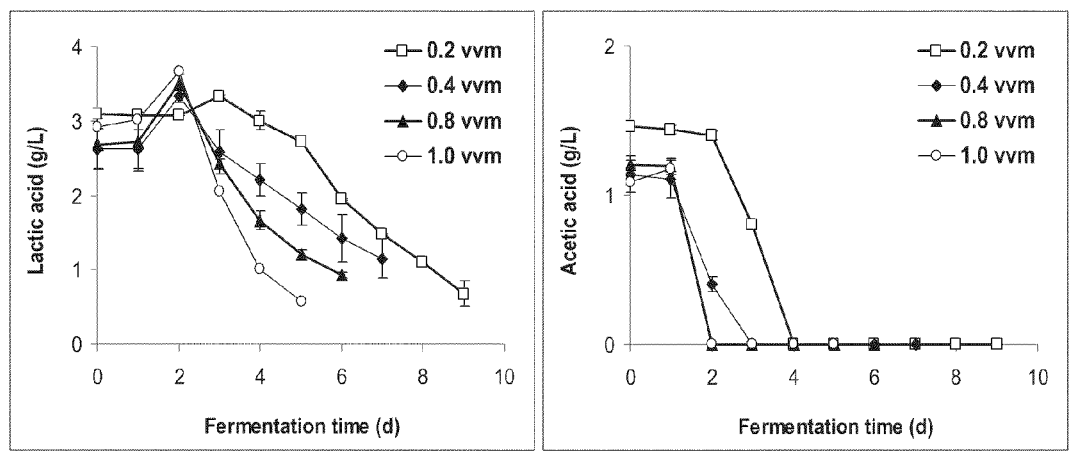
FIG. 12 illustrates lactic and acetic acid reductions during fungal cultivation of thin stillage in batch stirred bioreactors (5 L) with increasing aeration rates of 0.2 to 1.0 vvm. (n=2).

Initial lactic and acetic acids concentrations in fresh thin stillage ranged from 1.5-3.1 g/L and 1.0-1.5 g/L, respectively. The glycerol content in thin stillage was high, from 12.8 and 15.9 g/L. Organic acid production is primarily from bacterial contamination. Glycerol accumulation is a byproduct of yeast fermentation under stressed conditions [7]. In bench- and pilot-scale bioreactors, fungal removal of lactic acid, acetic acid, and glycerol tended to improve with increasing aeration rates. Lactic acid contents in bench-top bioreactor samples increased during the first 2 days of fungal cultivation (FIG. 12). This trend may indicate that the fungus was producing lactic acid initially. Several *Rhizopus* strains are known to produce lactic acid in submerged cultures [8]. From day 2 onward, lactic acid concentrations decreased, with reductions of 14, 31, 54, and 71% with aeration of 0.2, 0.4, 0.8, and 1.0 vvm, respectively, by day 5. Fermentation of soybeans with *R. oligosporus* for tempeh production confirms that this fungal species is able to degrade lactic acid [9].

Fungal cultivation of settled thin-stillage supernatant improved lactic acid biodegradation, with 60% removal in 5 days with 0.8-vvm aeration (as compared to 54% with thin stillage particles). Lactic acid reductions were substantially higher in the 50-L bioreactor, reaching 100% in 6 days with 0.2-vvm aeration and in 4 days with 1.0-vvm aeration, which may be related to better DO transfer.

Acetic acid removals also improved with increasing aeration rates. Complete removal was achieved in 4 days with aeration of 0.2 vvm, in 3 days with 0.4 vvm, and in 2 days with 0.8 and 1.0 vvm. Similar results were obtained using the settled thin-stillage supernatant with 100% removal in 2 days with 0.8-vvm aeration. In the 50-L fungal cultivations, the acetic acid removal was more rapid with 100% removal by day 2 with 0.2-vvm aeration and by day 1 with 1.0-vvm aeration.

Figure 13:
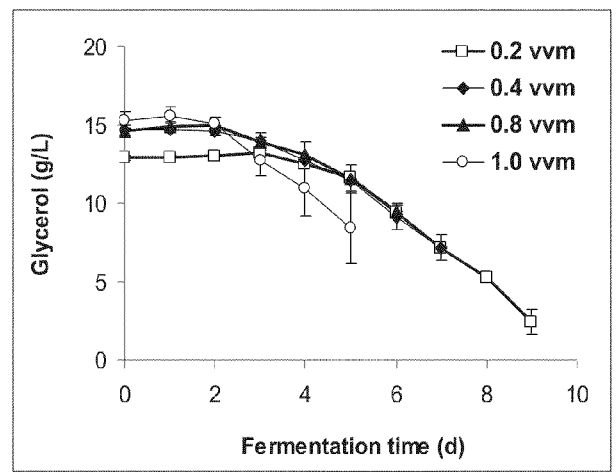
FIG. 13 illustrates glycerol reductions during fungal cultivation of thin stillage in batch stirred bioreactors (5 L) with increasing aeration rates of 0.2 to 1.0 vvm. (n=2).

Glycerol biodegradation in the thin stillage began 2 days after fungal inoculation (FIG. 13). This delay may be associated with the time required for the fungal culture to grow from spores. Reductions in glycerol concentrations by day 5 reached 11% with aeration of 0.2 vvm, 22% with 0.4 and 0.8 vvm, and 45% with 1.0 vvm. Degradation of glycerol increased to 33% in 5 d with settled thin-stillage supernatant (0.8-vvm aeration), compared to 22% with thin stillage particles present.

Glycerol reduction in 50-L bioreactors was significantly better with 100% removal achieved in 6 days with 0.2-vvm aeration and 5 days with 1.0-vvm aeration, which again suggests better oxygen transfer in the 50-L compared to the 5-L experiments.

3.5. Fungal Biomass Production

Quantifying fungal biomass production was complicated by the removal of thin stillage solids via attachment to the vessel wall above the liquid level and to the fungal mycelia. Thin stillage particles attached to the surface of the fungal biomass and within it, particularly inside the mycelia on the agitator blades. The final biomass weights provided in Table 1.1 include the freeze-dried fungal biomass and attached thin stillage solids, which were collected at the end of the experiments. The harvested biomass tended to increase with increasing aeration rates.

TABLE 1.1

Comparison of biomass production during fungal cultivation of thin stillage in stirred bioreactors (5 L) at increasing aeration rates.

| Air flow (vvm) | Cultivation period (d) | Final biomass (g dry wt/L)[a] |
|---|---|---|
| 0.4 | 7 | 27 ± 3 |
| 0.8 | 6 | 30 ± 3 |
| 1.0 | 6 | 36 ± 4 |

(n = 3)
[a]Weight of freeze-dried biomass, including fungal mycelia and attached thin stillage solids.

The experiment performed on the soluble-fraction of thin stillage had lower biomass production (13 g/L), in part since no thin stillage suspended solids were present to attach to the mycelia. The resulting yield was 0.43 g dry fungal biomass/g SCOD removed. Assuming a similar yield for the thin stillage with particles, the fungal biomass production in 6 days with 0.8-vvm aeration would be approximately 14 g/L based on SCOD reductions. The initial thin stillage suspended solids was 20 g/L, and the final biomass production was 30 g/L (an increase of 10 g/L). The lower actual biomass increase of 10 g/L compared to the expected fungal growth of 14 g/L, based on SCOD removal, confirms that suspended solids were both removed by attachment to the fungal biomass and by biodegradation to carbon dioxide and water. In the 50-L cultivation with 1.0-vvm aeration, more of the fungal mycelia and thin stillage solids remained in suspension. The production of 28 g dry biomass/L thin stillage was lower than obtained in the bench-top bioreactors, in part because centrifugation did not recover as much of the thin stillage solids as attachment to fungal mycelia.

3.6. Fungal Protein and Amino Acids

The average crude protein content of *R. microsporus* mycelia grown in YM broth for inoculation of the 50-L cultivations was 39% (w/w). The fungal biomass cultivated on the settled thin-stillage supernatant (no suspended solids) had up to 43% (w/w) crude protein. This fungal protein could be fed to nonruminants, swine and poultry.

Figure 14:
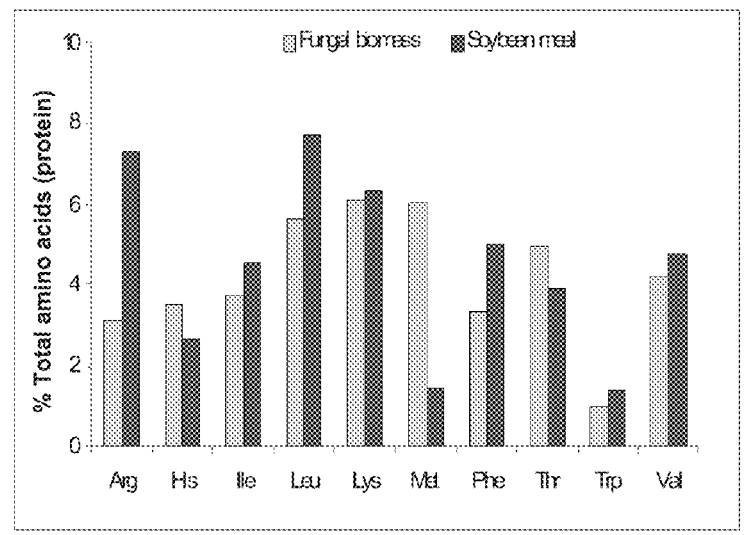
FIG. 14 illustrates essential amino acid composition of fungal biomass, cultivated in settled thin stillage supernatant, and soybean meal as a percent of protein (see Reference [11] of the described Example).

Lysine, methionine, tryptophan, and threonine are the main amino acids of concern for nonruminants [10]. Lysine and methionine are usually the first-limiting amino acids in corn-soybean meal diets for swine and poultry, respectively. Based on the amino acid data in Table 1.2, the dried fungal biomass had almost two-thirds the lysine and over 2.5 times the methionine contents of soybean meal (% as-fed basis). The fungal lysine, threonine, and tryptophan contents, however, were all comparable to soybean meal on a percent of protein basis (FIG. 14). Biomass protein contents and digestibility depend on harvesting, dewatering, and drying methods, as well as amounts of enmeshed stillage solids. Improved dewatering should increase the protein fraction (%) of the fungal biomass and, consequently, the lysine content (% as-fed). Water reclamation and fungal protein content may be enhanced by supplementing thin stillage with readily-bioavailable inorganic nitrogen sources.

TABLE 1.2

Amino acid composition of biomass on as-fed basis (10% moisture)

| Amino acid | Fungal biomass[a] (%) | Soybean meal[b] (%) | Corn[b] (%) | DDGS[b] (%) |
|---|---|---|---|---|
| Lysine | 1.8 | 3.0 | 0.3 | 0.6 |
| Methionine | 1.8 | 0.7 | 0.2 | 0.5 |
| Threonine | 1.5 | 1.9 | 0.3 | 1.0 |
| Tryptophan | 0.3 | 0.7 | 0.1 | 0.3 |

[a]Freeze-dried fungal biomass product includes enmeshed thin stillage solids.
[b]Data from NRC (1998) [11]

4. Conclusions

Fungal treatment of thin stillage in corn ethanol plants is an innovative technology to reclaim water, save energy and potentially enzymes, and produce an additional valuable coproduct. Recycling fungal-treated water directly could provide substantial energy savings by avoiding the current practice of evaporating and condensing water from thin stillage. The high-protein fungal biomass produced could be fed to nonruminants. The fungal biomass could also be used as raw material for the extraction of valuable biochemicals, such as chitosan. Fungal cultivation of thin stillage has the potential to make ethanol production more energy efficient and more sustainable, to reduce costs, and to produce an additional value-added co-product.

REFERENCES

[1] Renewable Fuels Association (RFA). Growing innovation: America's energy future starts at home. 2009 Ethanol Industry Outlook. Washington D.C.; 2009.
[2] Dunn, L. Personal communication through Lincolnway Energy, LLC; 2008.
[3] RFA. Industry resources: Coproducts. Accessed Oct. 1, 2009. http://www.ethanolrfa.org/industry/resources/coproducts/.
[4] Antai S P, Crawford D L. Degradation of softwood, hardwood, and grass lignocelluloses by two *Streptomyces* strains. Appl Environ Microbiol 1981; 42:378-80.
[5] Dubois M, Gilles K A, Hamilton J K, Rebers P A, Smith F. Colorimetric method for determination of sugars and related substances. Anal Chem 1956; 28(3):350-56.
[6] Kunduru M R, Pometto III A L. Continuous ethanol production by *Zymomonas mobilis* and *Saccharomyces cerevisiae* in biofilm bioreactors. J Ind Microbiol 1996; 16:249-56.
[7] Walker G M. Yeast physiology and biotechnology. Chichester, UK: Wiley & Sons; 1998.
[8] Zhang Z Y, Jin B, Kelly J M. Production of lactic acid from renewable materials by *Rhizopus* fungi. Biochem Eng J 2007; 35:251-63.
[9] Sparringa R A, Owens J D. Causes of alkalinization in tempe solid substrate fermentation. Enzyme Microb Technol 1999; 25:677-81.
[10] Cheeke P R. Applied animal nutrition: Feeds and feed. New Jersey, USA: Pearson Education, Inc.; 2005.
[11] National Research Center (NRC). Nutrient requirements of swine. 10th Ed. Washington D.C.: National Academies Press; 1998.

Example 2

Fungal Treatment of Thin Stillage in Airlift Reactors

Airlift reactors represent an efficient way of introducing oxygen at high rates. Extremely high rates of oxygen transfer may be required for the aerobic fungal process along with the particularly high oxygen demand of thin stillage from corn-to-ethanol plants. Three different airlift reactors were constructed on different scales to develop design guidelines for effective aeration.

2.1 Airlift Reactor of 6 L

Figure 15:
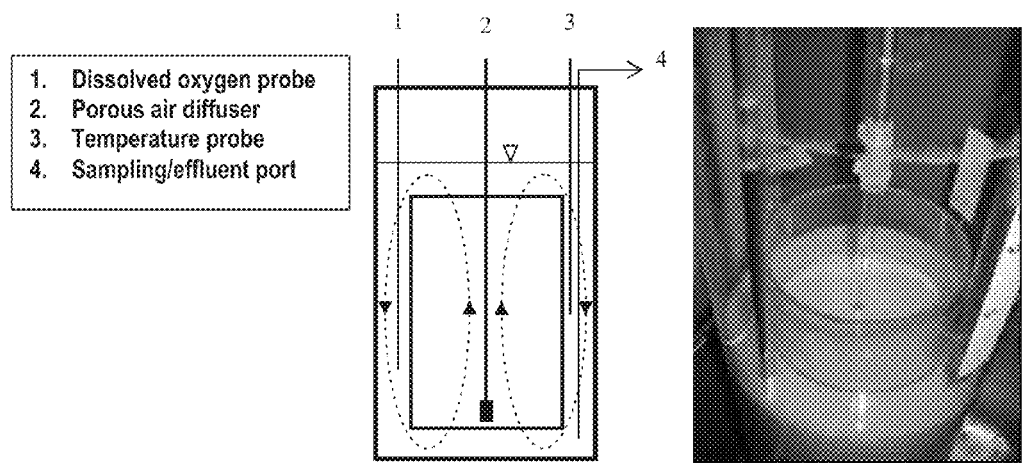
FIG. 15 is a schematic of a draft-tube reactor (5 L), showing aeration created liquid movement with arrows (left), and a photo of a draft-tube reactor setup and aseptic addition of thin stillage (right).
Figure 16:
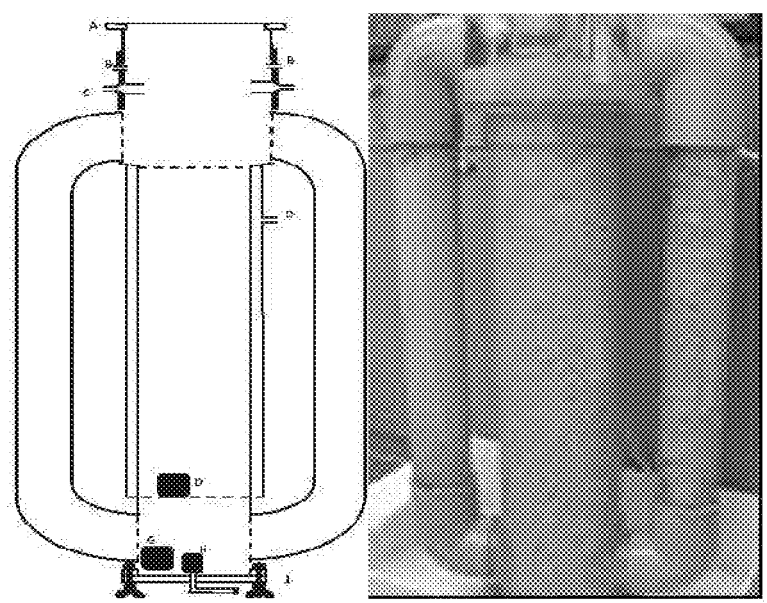
FIG. 16 is a schematic of an airlift reactor with external recirculation tubes and a photo of the reactor in action.
Figure 17:
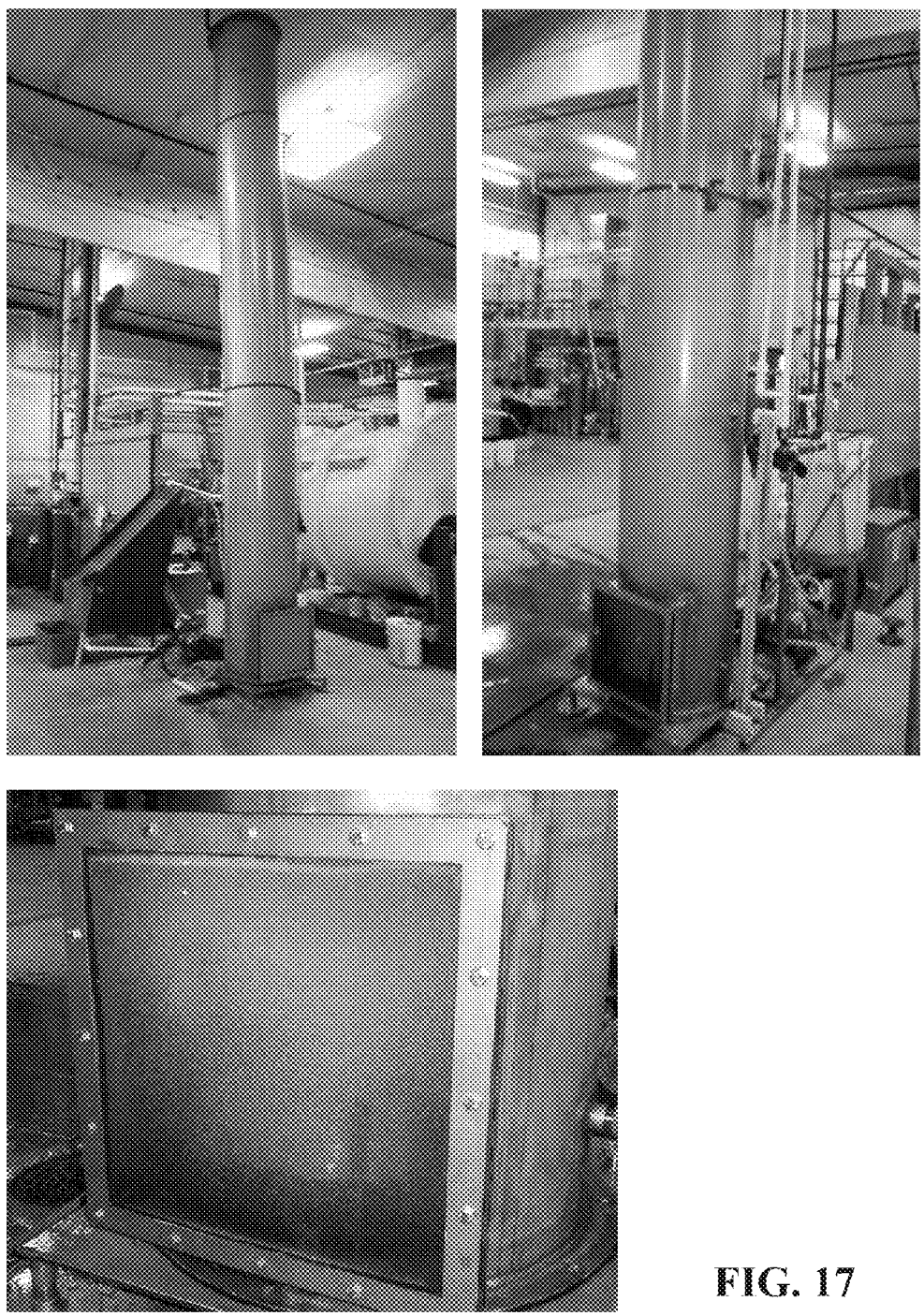
FIG. 17 illustrates an airlift pilot plant reactor showing the height of the column, some of the pipework for aeration and recirculation and the view pane showing the air bubbles from aeration.

An airlift reactor was constructed by fitting a 100 mm draft tube inside a 150 mm reactor, vertically and concentric with the main reactor. This draft tube was shorter than the main reactor and mounted such that the reactor contents could freely flow between the inner part of the draft tube and the annulus between the draft tube and the reactor. This stillage with a fungal inoculum was added to the reactor similar to what was done in Example 1. The reactor was aerated only in the center portion, causing the contents to expand and move upwards along with the air bubbles. This also causes the reactor contents to flow downward in the annulus (See FIG. 15).

2.2 Airlift Reactor with External Recirculation (25 L)

A new type of airlift reactor was developed with external draft tubes (see FIGS. 4A-C and 16).

The reactor could be aerated in the central part, the contents move upwards, and air bubbles separate in the wider section at the top, while the content without bubbles moves through the external recirculation tubes. There was also a water jacket for passing heated water through to maintain the temperature in the reactor at 37° C.

2.3 Pilot-Scale Airlift Reactor

A pilot-scale airlift reactor was constructed of 20' tall and 2' in diameter with an internal draft tube, in a similar configuration as the 6 L reactor. This column has an available volume of 350 gal or about 1300 L. Aeration is provided through a porous diffuser of 19" in the bottom. Fungal harvesting is done by recirculating the suspended fungal mass through a screen with openings of $\frac{1}{8}^{th}$ of an inch. The screen is mounted on top a 15 gal tank into which the water drains and recirculated from there by pump. The excess fungal pellets are collected as they fall from the edge of the screen.

2.4 Sample Analysis

Feed thin stillage and reactor samples were analyzed for total and soluble chemical oxygen demand (TCOD, SCOD), total and volatile suspended solids (TSS, VSS), nitrogen content, total and reducing sugars, lactic and acetic acids, and glycerol. The COD and suspended solids analyses were performed as described in Standard Methods (APHA/AWWA/WEF, 2005). Analysis of lactic and acetic acids and glycerol was performed with high pressure liquid chromatography.

2.5 Results and Discussion

Figure 18:
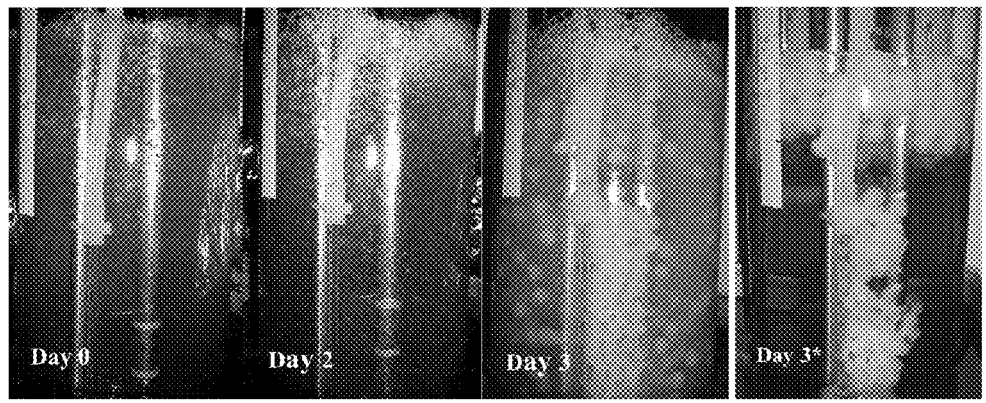
FIG. 18 illustrates fungal cultivation of settled thin stillage supernatant in an airlift draft-tube reactor with 1.0 vvm aeration on the day of spore inoculation (day 0) through day 3. *Mycelia floated when aeration was off.
Figure 19:
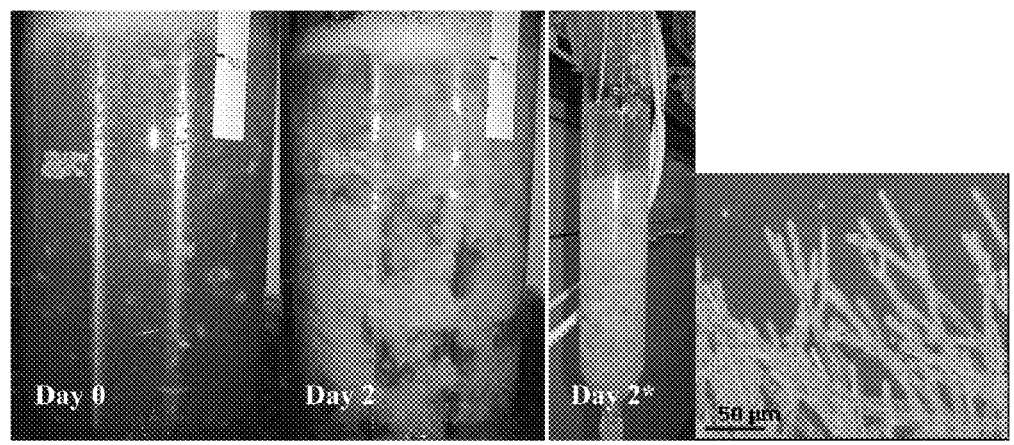
FIG. 19 illustrates fungal cultivation of settled thin stillage supernatant (4.5 L) in an airlift draft-tube reactor with 1.5 vvm aeration. *Mycelia settled on day 2 when pumped into a 500-ml buret. Additionally shown is a microscope photo at a bar length of 50 μm.

Fungal growth and morphology depended on aeration rates in airlift experiments. Small fungal pellets were observed within 2 days of spore inoculation during fungal cultivation of the settled thin stillage supernatant at 1.0 vvm aeration (FIG. 18). The spherical pellets grew in size and filled the reactor by day 3. Suspended fungal pellets floated when aeration was turned off (FIG. 18, Day 3*). Mycelia inoculation of settled thin stillage supernatant, in place of spores, and a higher aeration rate of 1.5 vvm resulted in rapid fungal growth (FIG. 19). Fungal mycelia filled the reactor within 2 days of inoculation. The mycelia growth can be seen on the microscope photo.

Organics (COD) Removal.

The SCOD was reduced by 46% in 5 days with aeration rates 0.8 vvm. The DO saturation level at 0.8 vvm, the optimal rate for SCOD reduction in 5-L reactors, dropped from 100% saturation to 3% in 2 days. The 50 L stirred fungal reactor SCOD decreased by 71% in 4 days at 1.0 vvm due to the more rapid start-up from mycelia inoculums and better oxygen transfer. The broth was very dense by day 4 at 1.0 vvm, DO level averaged only 1% saturation from day 1. Effective separation of suspended solids from the effluent result in TCOD removals of 75 and 84% in 5 days for 0.2 and 1.0 vvm aeration rates.

Figure 20:
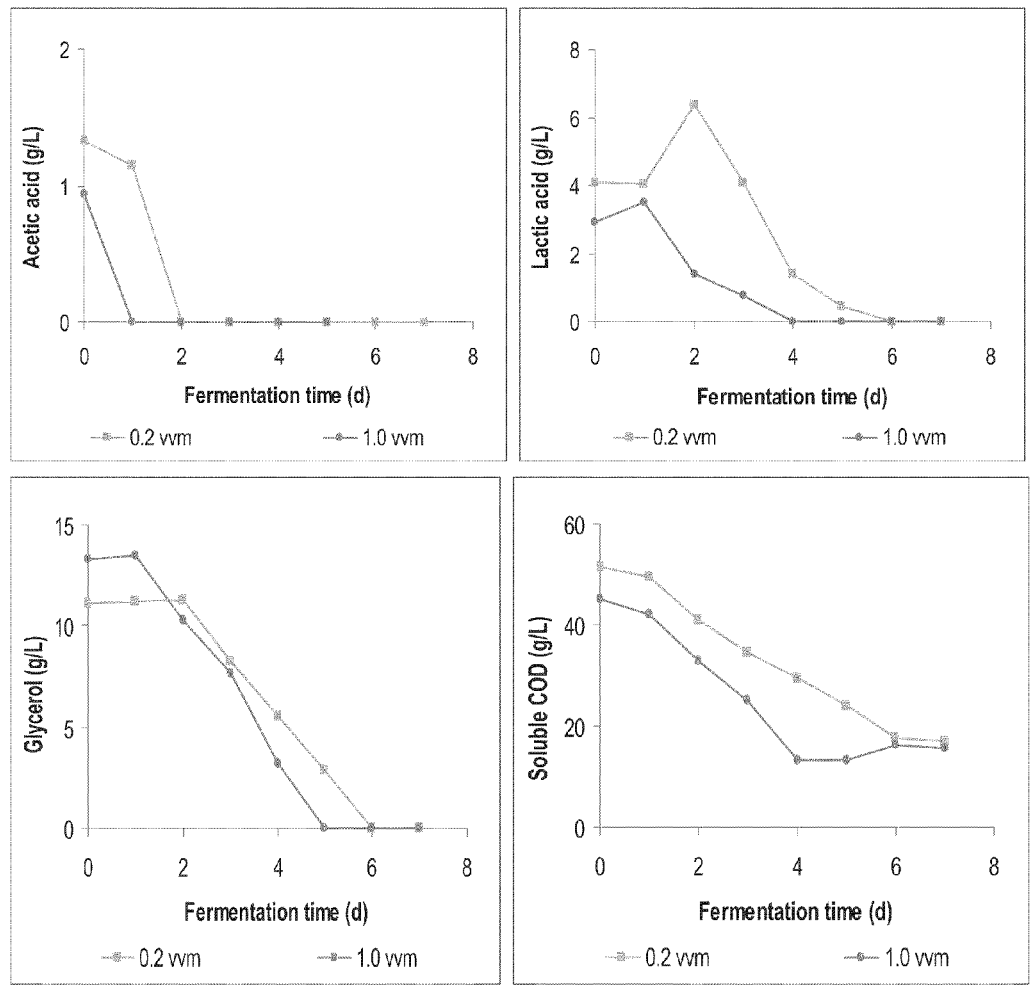
FIG. 20 illustrates acetic acid, lactic acid, glycerol and soluble COD removal.

Organic acids and glycerol removal were achieved as follows: Acetic acid 100%, lactic acid 90%, 80% glycerol removal was achieved (see FIG. 20).

Fungal Biomass Production.

The yield was 0.43 to 0.45 g dry fungal biomass/g SCOD removed. The average protein content of *R. microsporus* mycelia was 39%. The fungal biomass cultivated on the settled thin stillage supernatant (no thin stillage suspended solids) had 35% protein. Slightly higher biodegradation of SCOD was achieved by day 3 with 1.5 vvm aeration (29%) as compared with 1.0 vvm (25%). The higher reduction (25%) with thin stillage suspended solids supports the stirred fungal reactor findings that the particles provided a nutrient that enhanced fungal growth.

Suspended Solids Removal.

Total and volatile suspended solids contents were similar in all experimental samples, indicating low levels of fixed, inorganic suspended solids. The suspended solids concentrations decreased by 99%, mainly towards the end of the fungal growth period. Suspended solids in the thin stillage were removed by attachment to fungal mycelia and by biological mineralization. Liquid collected from the stirred reactor effluent port was well-clarified, as low as 20 mg/L suspended solids, with a yellow tint (FIG. 21). Solids separation before returning the water to the corn fermentation tanks important was achieved, avoiding build-up of non-degradable substances. The effluent could, based on known limitations, be recycled as is.

Reactor with External Recirculation Results.

The 25 L reactor with external recirculation showed more effective recirculation, oxygen transfer and easily harvestable (course screening) and dewaterable large pellet growth (FIG. 22).

2.6 Conclusion

An innovative technology based on fungal treatment/cultivation has been developed to reclaim water at ethanol plants, save energy and enzymes and produce additional valuable byproducts. This would make ethanol production from corn much more energy efficient and therefore more sustainable. This process would reduce costs and make an important part of the biofuel industry much more environment friendly. Expanding ethanol plants into applications of this technology would create new jobs and rural prosperity. The technology has potential for adaptation in other industrial wastewater applications and to reduce the complexity and energy expenditure of current approaches, particularly in the food industry.

Example 3

Development of Oil Recovery Technology

The oil production process involves the oleaginous mold, *Mucor circinelloides*, which is able to produce and accumulate triglycerides to constitute over 60% of its cell mass when grown on simple carbon sources. These carbon sources could be left-over carbohydrate wastes from other plant processing activities and that is a viable option to extend biofuel production at existing facilities where crops are processed. The oil is in the form of triglycerides. Ultrasonication, in the presence of methanol or ethanol and a recyclable catalyst transesterifies the oil to mycofuel, akin to biodiesel. A new catalyst makes this possible in seconds and at low pressure and energy expenditure. This contrasts industrial techniques that require nearly an hour of reaction time at elevated temperatures (~60 C). Glycerol byproduct from the mycofuel formation can be recycled and used as additional substrate in the *Mucor circinelloides* reactor to make more fungal oil. A more detailed description follows.

3.1 The Oleaginous Fungal Oil Production

All microorganisms are able to synthesize lipids for essential functioning of their membranous structures. However, a few microbes in the microbial kingdom accumulate more than 20% lipids in their cells. These microbes, so-called oleaginous organisms, including algae, yeasts and molds, store lipid in oil vacuoles in the form of triacylglycerides.

The physiology of lipid overproduction is cultivation of oleaginous microorganisms on a medium with an excess of carbon and a limited quantity of other important nutrients, especially inorganic nitrogen. Important for the lipid accumulation mechanism in oleaginous microorganisms is the presence of one of the key enzymes of lipogenesis, namely, ATP:citrate lyase (ACL), which provides acetyl-CoA by the cleavage of citrate (Botham and Ratledge, 1979). Microorganisms without this enzyme appear to be unable to achieve the same degree of lipid accumulation as those that possess it. The initial and rate-limiting step of fatty acid biosynthesis, catalyzed by acetyl-CoA carboxylase (ACC), is the ATP-dependent conversion of acetyl-CoA to malonyl-CoA, the two-carbon donor for fatty acid chain extension.

The formation of the reducing agent NADPH, essential for the conversion of the acetyl-CoA into fatty acids must be facilitated. Several pathways produce NADPH in cells growing on glucose. It is generated primarily via the oxidation of glucose 6-phosphate in the pentose phosphate cycle by glucose 6-phosphate dehydrogenase and 6-phospho-gluconate dehydrogenase. Malic enzyme was shown to be an important source of NADPH for lipid accumulation in oleaginous yeasts (Evans and Ratledge, 1985) and filamentous fungi (Wynn and Ratledge, 1997; Wynn et al., 1997) as well as for fungal fatty acid desaturation reactions (Kendrick and Ratledge, 1992). However, the oxidation of cytosolic isocitrate by NADP-isocitrate dehydrogenase also contributed to NADPH generation in lipid-accumulating yeasts (Sokolov et al., 1995).

Although lipogenesis comprises all metabolic steps from glucose to triacylglycerides, attention has mostly focused on the enzymes that catalyze the formation of a two-carbon precursor for fatty acid synthesis and on the auxiliary systems donating NADPH. It is more than likely that more than one pathway may be engaged in this process, and which pathway is used varies with the developmental stage and cultivation conditions of the microbial species, and the type of microbial species. The nature and concentration of the nitrogen source used in the medium is an essential factor regulating lipogenesis. Many reports have appeared concerning various nitrogen sources employed for fungal fatty acid production (Certik et al., 1993; Kolesnikova and Tolstikova, 1984; Moreton, 1988). Fungi produce oil globules that are readily seen under the microscope (see FIG. 23).

3.2 Myco-Fuel from High-Strength Organic Wastewater or Co-Product Streams

Figure 24:
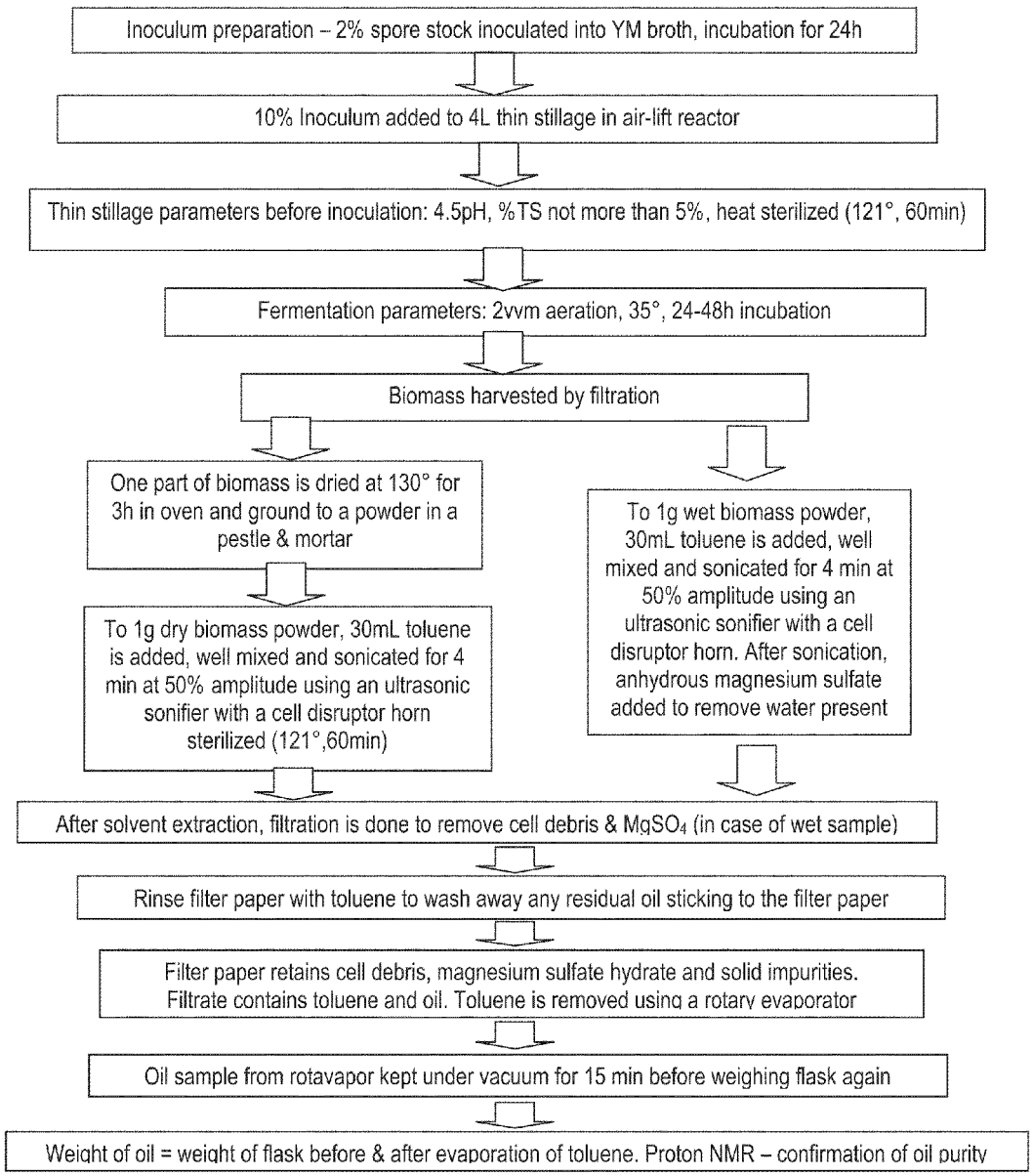
FIG. 24 illustrates Table 3.1, showing the protocol for *Mucor* fermentation in thin stillage and oil recovery.
Figure 25:
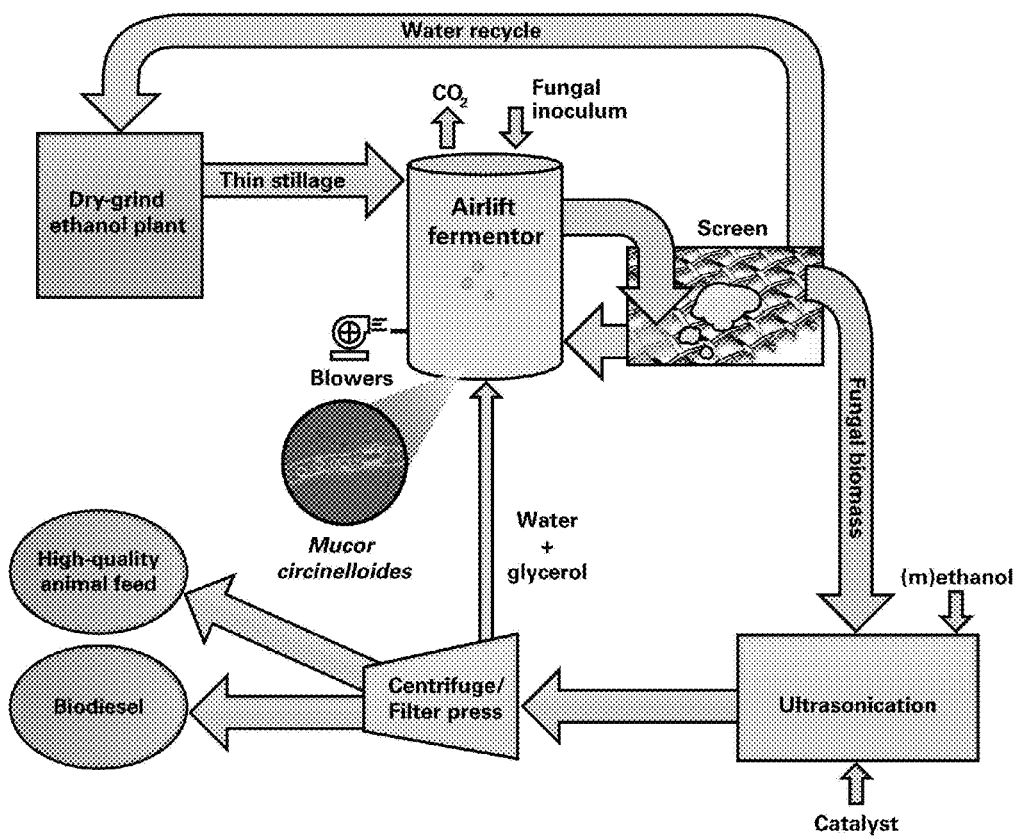
FIG. 25 illustrates the myco-fuel process based on corn-to-ethanol leftover thin stillage as feed.

In its simplest application, the Mycofuel process involves cultivation of *Mucor circinelloides* in high-strength organic co-products streams from biofuel production or food production and using the lipids produced as a raw material to produce biodiesel, or more specifically, mycofuel. Both thin stillage, a left-over product from the dry-grind corn-to-ethanol process and soy whey from soy protein isolate (tofu) production are good substrates. Key to successful lipid synthesis and accumulation is control over nutrients, particularly inorganic nitrogen. The cultivation and oil determination on flask scale is outlined in Table 3.1 (FIG. 24). The oil determination part can also be used to measure oil content on larger-scale applications. The commercial Mycofuel process based on thin stillage is shown in FIG. 25. The fungal biomass is easily harvested by screening due to its filamentous nature.

Table 3.2 makes a comparison between the fungal technology and other microbial biofuel production alternatives.

TABLE 3.2

Comparison of bioprocess requirements

| Bioprocess | Mycofuel | Biodiesel | Ethanol | Bioethanol |
|---|---|---|---|---|
| Organism | Wood-rot and oleaginous fungi | Plants | Yeasts | Yeasts |
| Substrate | Carbohydrates from plants | Lipids from plant synthesis | Sugar from starch | Sugar from lignocellulosics |
| Oxygen needs | Aerobic | Photosynthesis | Anaerobic | Anaerobic |
| Enzyme needs | Produced in-situ | None required | External enzymes | External enzymes |

The fungal cells, after harvesting, can be destroyed by ultrasonication to release the oil. However, when methanol or ethanol is present along with a heterogeneous catalyst developed in our group, transesterification occurs in the same reactor and is accelerated by the ultrasonication without the elevated bulk temperatures otherwise required. This technology has been demonstrated in other fields of science to accelerate reaction rates manifold. Plasma can be generated with ultrasonics and are made visible through luminance produced. While these lights re beautiful, the real benefit is that ultrasonication renders mycofuel directly, which then only needs to be separated by physical procedures, involving a combination of centrifugation and filtration to also separate the high-quality animal feed from the water-containing glycerol. The ultrasonic energy enhances the reaction kinetics and releases the oil by the same processes used in ultrasonic cleaners; namely cavitation and streaming. The cavitation, similar to the cavitation that promotes erosion of boat propellers, releases tremendous shear forces during a violent impulsion at the end of their life. These shear forces break up nearby cells, particles and increase reaction sites for chemical reactions. The streaming process also helps mix the reactants to increase the reaction rates. In addition, the glycerol is beneficially recycled with the water to the fungal process, where it serves as an additional substrate for fungal cultivation. Most important are the short reaction times and low energy inputs. Table 3.3 compares ultrasonication as a means of ultrasonically assisted transesterification with other biodiesel production methods.

The fungal biomass is easily harvested by screening due to its filamentous nature. The fungal cells can then be destroyed by ultrasonication to release the oil. However, when methanol or ethanol is present along with a heterogeneous catalyst, transesterification occurs in the same reactor and is accelerated by the ultrasonication without the elevated bulk temperatures otherwise required. This technology has been demonstrated to accelerate reaction rates manifold. Plasma can be generated with ultrasonics and are made visible through luminance produced. While these lights are beautiful, the real benefit is that ultrasonication renders myco-fuel directly, which then only needs to be separated by physical procedures, involving a combination of centrifugation and filtration to also separate the high-quality animal feed from the water-containing glycerol. The ultrasonic energy enhances the reaction kinetics and releases the oil by the same processes used in ultrasonic cleaners; namely cavitation and streaming. The cavitation, similar to the cavitation that promotes erosion of boat propellers, releases tremendous shear forces during a violent impulsion at the end of their life. These shear forces break up nearby cells, particles and increase reaction sites for chemical reactions. The streaming process also helps mix the reactants to increase the reaction rates. In addition, the glycerol is beneficially recycled with the water to the fungal process, where it serves as an additional substrate for fungal cultivation. Most important are the short reaction times and low energy inputs.

The present technology employs a robust, highly recyclable heterogeneous catalyst (Chintareddy et al., 2007) that has been shown to efficiently catalyze the conversion of fungal triglycerides to mycofuel. The catalyst consists of a strong polymeric backbone to which robust catalytic sites are strongly chemically bonded. These catalytic sites are based on compounds that were invented at Iowa State University and are commercially available from several vendors in the US and Europe. In contrast to industrial catalysts for the production of biodiesel, our catalyst is uniquely environmentally benign because it requires no heating to operate efficiently, it can be recycled many times, and it contains no metals. The catalyst is very insoluble and it is easily adapted to batch or flow-through operations.

TABLE 3.3

Comparison of ultrasonication with current procedures

| Ultrasonication | Ultrasonic Enhanced Production | Current technology |
|---|---|---|
| Reaction time | <1 min. | 40-80 min. |
| Reaction temperature | 25-30° C. | 60-70° C. |
| Est. energy consumption | 80-120 kJ/L | 120-160 kJ/L |
| Capital costs | High | Medium |
| Operating costs | Medium | High |
| Process mode | Continuous | Batch |
| Catalysts | Hetero/Homogeneous | Heterogeneous |

Table 3.4 lists catalyst systems reported in the literature that can be used for plant oil transesterification. It is well known that alkaline alkoxides and hydroxides (Entry 1) are considerably more effective as catalysts than acid catalysts (Entry 2), operate at lower temperatures and are widely used industrially. However, plant oils with high free fatty acid contents suffer soap formation in the presence of homogeneous alkaline catalysts, leading to product loss and problems with product separation and purification. Metal complexes (Entry 3) suffer from environmentally toxicity issues and enzymes (Entry 4) operate very slowly. Although some of these protocols afford good biodiesel yields (Shah, 2004; Dorado, 2004; Abreu, 2003, 2004) all have one or more disadvantages such as lack of catalyst reusability (hence producing waste streams), handling difficulties, the need for elevated temperatures requiring energy, multi-step catalyst synthesis and most importantly, frequent problems with adaptability to large-scale preparations.

TABLE 3.4

Reported routes for the transesterification of plant oils to biodiesel

| Entry | |
|---|---|
| | Homogeneous catalysts |
| 1 | Alkaline metal hydroxides alkoxides |
| 2 | HCl, $H_2SO_4$ |
| 3 | Tin, lead, mercury and zinc complexes |
| 4 | Enzymes |
| | Heterogeneous catalysts |
| 5 | Polymer-bound guanidines, amines |
| 6 | $K_2O$, CaO, (including nano-crystalline CaO), MgO $ZrO_2$, and ZnO |
| 7 | $MgO/Al_2O_3$, $KNO_3/ZrO_2$ $TiO_2/SiO_2$, $K_2O/Al_2O_3$, $KNO_3/KI$ zeolite, $ZnO/Al_2O_3$, and $WO_3/ZrO_2$ |
| 8 | $SO_4^{2-}/SnO_2$, $SO_4^{2-}/ZrO_2$ $Fe/SO_4^{2-}/ZrO2$ |
| 9 | Ion exchange resins |
| 10 | 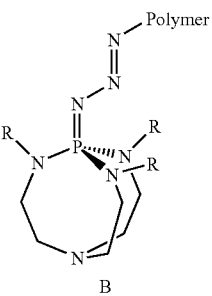 B |

Heterogeneous catalysts are advantageous for biodiesel production because of their reusability and consequently their more eco-friendly nature. Such catalysts can also lend themselves to easier product separation and better product purity, since water washes can be eliminated. Such catalysts anchored to organic polymers have been described, which operate at the reflux temperature of the alcohol employed (Schuchardt, 1996; Sercheli, 1999; Suppes, 2004). However, these approaches suffer from leaching of organic moieties from the catalytic sites on the support. Metal oxide systems have also been investigated as heterogeneous catalysts for biodiesel production (Xie, 2006; Reddy, 2006; Bournay, 2005). Such catalysts include single metal oxides (Entry 6), mixed metal oxides (Entry 7) and sulfated metal oxides (Entry 8). All of these catalyst systems require the use of elevated temperatures at some point and/or the necessity for periodic regeneration at high temperatures because of catalyst fouling by oil impurities and hydrolysis by adventitious moisture in the oil and/or methanol.

Anion exchange resins (Entry 9) such as Diaion PA308, PA306s and HPA25 have been reported to convert plant oils to biodiesel (Shibasaki-Kitakawa, 2007). All operate at ambient temperatures, but they also require periodic regeneration by a 3-step process. Sulfonated pyrolized carbohydrates have recently been employed successfully at elevated temperatures, but though this catalyst can be re-used, the number of cycles was not mentioned (Toda, 2005).

Polymer-supported non-metallic catalysts or reagents are attractive because of advantages they possess over homogeneous catalysts (e.g., recyclability, more simple product isolation, and reduction of environmental pollution) (Ley, 2000; Leadbeater, 2002). The literature contains numerous instances in which such systems have successfully replaced homogeneous catalysts in organic transformations (Drewry, 1999, McNamara, 2002) but they do not appear to have been used successfully for biodiesel production.

Organic bases exist which are sufficiently Lewis basic to cause adequate deprotonation of the methanol to methoxide ion (the actual catalyst in base-catalyzed transesterifications of plant oils to biodiesel). An adequate concentration of methoxide ion ($^-$OMe) allows rapid and complete transesterification at ambient temperature, thus saving energy. The novel polymer systems A in Entry 10 of Table 4, which we developed for this purpose are "pro-catalysts" (i.e., pre-cursors to $^-$OMe) which are unique in that they have a set of advantages that the other catalysts in Entries 1-9 lack:

1. They are hydrolytically stable to adventitious water present in the methanol and/or the feedstock oil.
2. They are thermally stable for long periods of time and stable fodr months on storage.
3. They are operated very efficiently at room temperature for biodiesel production (Chintareddy et al., 2007).
4. No further washing/purification of the soybean oil or glycerin we produce is required.
5. Catalyst leaching is not a problem.
6. B systems contain no metal to harm the environment.
7. B systems can be synthesized which resist coating/plugging by components (e.g., lipids) present in the oil.

3.3 Results with Oil Recovery and Production from Corn-to-Ethanol Thin Stillage

Fungi grown on thin stillage, in either shake flasks or airlift reactors, will typically result in a bio-mass yield of 20 to 30 g of biomass per liter of thin stillage, which incorporates about 30-40% oil. This is true for both *Rhizopus microsporus* and *Aspergillus oryzae*. The oil content with *Mucor circinelloides* cultivation is about 35-45%, higher due to fungal oil production, myco-oil, within the cells. All the other oil collected on the biomass from all three species is oil originating from corn.

The oil is readily separated by extraction with toluene, and much of it can be removed physically by first dewatering and drying followed by pressure filtration or centrifugation.

The oil yield achievable with *Rhizopus microsporus* and *Aspergillus oryzae* is 7-9 g/L, or 0.06-0.08 lb/gal thin stillage, which equates to 0.2 to 0.25 lb oil per gallon ethanol produced. The yield using *Mucor circinelloides*, including the myco-oil, is 0.25-0.33 lb/gal ethanol.

It was found that the oil recovered was mainly a triglyceride and that most of the lipids were linoleic acid, an 18 carbon unsaturated fatty acid. This would have nutritional benefits, particularly for poultry. More importantly, it was found that after dewatering, drying and ultrasonication, the oil was easily transesterified with methanol using the heterogeneous catalyst described above, rendering a good quality of biodiesel.

3.4 Improvement on Competitive Technologies

The fungal process disclosed herein involves the use of a unique mold that will convert simple carbohydrates to oils, much more cost effectively than farming and processing oil seeds. This can be expanded to much larger opportunities to make cellulosic biofuels. The oleaginous fungal unit process synthesizes oil from low-cost substrates and there is no other technology to synthesize oils other than experimental algal based processes. The latter typically need light and, if solar based, huge areas and face significant water losses through evaporation. Ultrasonics are synergistically used to improve oil separation and to increase the activity of a novel catalyst for enhancing mycofuel production. The cycle times are reduced from the conventional 45-60 minutes at 60° C. to ambient temperatures in less than a minute. This not only results in much smaller equipment but also a great reduction in energy consumption during the production of biofuels. This increases the overall efficiency of biofuel production.

Table 3.5 compares Mycofuel to other liquid fuel alternatives by way of conclusion.

TABLE 3.5

Comparison of automotive fuel properties and implications

| Liquid fuel | Mycofuel | Biodiesel | Bioethanol | Diesel/gasoline |
|---|---|---|---|---|
| Raw material | Various renewables | Oil seed plants | Ligno-cellosics | Petroleum |
| Fuel energy | High | High | Low | High |
| Wastes | Low | Medium | High | Low |
| Byproducts | Lignin, feed | Glycerol | Useless | Various |
| Sustainability | High | Marginal | Marginal | Low |
| Cost | Low | High | High | Variable |

3.5 Principal Applications of this Process

This process is an improved approach to producing biodiesel. The process revolutionizes the biofuels industry. Oils are energy dense—better fuels than ethanol—and oils from seed crops are readily converted to biodiesel. The approach is to break down lignocellulosic materials, such as crop residues, forestry wastes and grasses to sugars using ammonia delignification and in-situ produced fungal enzymes, and convert the sugars to oil using oleaginous fungi. Much research has focused on saccharification of cellulosic biomass into sugars for ethanol production, but this concept is plagued by prohibitive enzyme costs and a large energy demand for distillation of low ethanol concentrations. In short, the current ethanol approach being developed is not viable, as it is more expensive than what the ethanol is worth. By contrast, the approach described herein can be demonstrated to be not only viable, but quite profitable.

4. Conclusions

Fungal treatment of thin stillage in corn ethanol plants is an innovative technology to reclaim water, save energy and potentially enzymes, and produce an additional valuable co-product. Recycling fungal-treated water directly provides substantial energy savings by avoiding the current practice of evaporating and condensing water from thin stillage. The high-protein fungal biomass produced could be fed to nonruminants. The fungal biomass could also be used as raw material for the extraction of valuable biochemicals, such as chitosan. Fungal cultivation of thin stillage has the potential to make ethanol production more energy efficient and more sustainable, to reduce costs, and to produce an additional value-added co-product. It is contemplated that fungal cultivation of thin stillage will focus on improving the mode of aeration in order to reduce the treatment time, such as employing an airlift design, and producing biomass on a pre-commercial scale.

REFERENCES

[1] Renewable Fuels Association (RFA). Growing innovation: America's energy future starts at home. 2009 Ethanol Industry Outlook. Washington D.C.; 2009.
[2] Dunn, L. Personal communication through Lincolnway Energy, LLC; 2008.

[3] Schaefer S H, Sung S. Retooling the ethanol industry: Thermophilic anaerobic digestion of thin stillage for methane production and pollution prevention. Water Environ Res 2008; 80(2):101-8.

[4] Singh S, Fan M, Brown R C. Ozone treatment of process water from a dry-mill ethanol plant. Bioresour Technol 2007; 99(6):1801-5.

[5] RFA. Resource center: How ethanol is made. Accessed Oct. 1, 2009. http://www.ethanolrfa.org/resource/made/.

[6] RFA. Industry resources: Coproducts. Accessed Oct. 1, 2009. http://www.ethanolrfa.org/industry/resources/co-products/.

[7] Wicking, J B. Personal communication through Biovance Zwam, Inc.; 2009.

[8] Sankaran S, Khanal S K, Pometto III A L, van Leeuwen J (Hans). Use of filamentous fungi for wastewater treatment and production of high value fungal byproducts: A review. Crit. Rev Env Sci Biotechnol 2010; (in press).

[9] Van Leeuwen J (Hans), Hu Z, Yi T, Pometto III A L, Jin B. Kinetic model for selective cultivation of microfungi in a microscreen process for food processing wastewater treatment and biomass production. Acta Biotechnol 2003; 23(2-3):289-300.

[10] Van Leeuwen J (Hans), Shrestha P, Rasmussen M L, Nitayavardhana S, Khanal S K. Value-added processing of residues from biofuel industries. Chapter 18. In: Khanal S K, editor. Biofuel and bioenergy from biowastes and residues, To be published by American Society of Civil Engineers (ASCE).

[11] Dhiraj A, Vattem A, Shetty K. Solid-state production of phenolic antioxidants from cranberry pomace by *Rhizopus oligosporus*. Food Biotechnol 2002; 16(3):189-210.

[12] Gautam P, Sabu A, Pandey A, Szakacs G, Soccol C R. Microbial production of extracellular phytase using polystyrene as inert solid support. Bioresour Technol 2002; 83(3):229-33.

[13] Jin B, van Leeuwen J (Hans), Doelle H W. The influence of geometry on hydrodynamic and mass transfer characteristics in a new external airlift reactor for the cultivation of filamentous fungi. World J Microbiol Biotechnol 1999; 15:73-9.

[14] Nahas E. Control of lipase production by *Rhizopus oligosporus* under various growth conditions. J Gen Microbiol 1988; 134(1):227-33.

[15] Sutardi, Buckle K A. Characterization of extra- and intracellular phytases from *Rhizopus oligosporus* used in tempeh production. Int J Food Microbiol 1988; 6(1):67-79.

[16] Yanai K, Takaya N, Kojima N, Horiuchi H, Ohta A, Takagi M. Purification of two chitinases from *Rhizopus oligosporus* and isolation and sequencing of the encoding genes. J Bacteriol 1992; 174(22):7398-406.

[17] Jin B, van Leeuwen J (Hans), Patel B, Yu Q. Utilization of starch processing wastewater for production of microbial biomass protein and fungal α-amylase by *Aspergillus oryzae*. Bioresour Technol 1998; 66:201-6.

[18] Tan S C, Tan T K, Wong S M, Khorb E. The chitosan yield of zygomycetes at their optimum harvesting time. Carbohydr Polym 1996; 30(4):239-242.

[19] Rhodes R A, Hall H H, Anderson R F, Nelson G E N, Shekleton M C, Jackson R W. Lysine, methionine, and tryptophan content of microorganisms III. Molds. Appl Environ Microbiol 1961; 9(3):181-84.

[20] Jasti N, Khanal S K, Pometto III A L, van Leeuwen J (Hans). Fungal treatment of corn processing wastewater in an attached growth system. Water Practice Technol 2006; 1(3).

[21] Jasti N, Khanal S K, Pometto III A L, van Leeuwen J (Hans). Converting corn wet-milling effluent into high-value fungal biomass in an attached growth bioreactor. Biotechnol Bioeng 2008; 101(6):1223-33.

[22] Jasti N, Rasmussen M L, Khanal S K, Pometto III A L, van Leeuwen J (Hans). Influence of selected operating parameters on fungal biomass production in corn ethanol wastewater. J Environ Eng 2009; (in press).

[23] Jin B, van Leeuwen J (Hans), Patel B, Doelle H W, Yu Q. Production of fungal protein and glucoamylase by *Rhizopus oligosporus* from starch processing wastewater. Process Biochem 1999; 34(1):59-65.

[24] Jin B, van Leeuwen J (Hans), Patel B, Yu Q. Mycelial morphology and fungal protein production from starch processing wastewater in submerged cultures of *Aspergillus oryzae*. Process Biochem 1999; 34(4):335-40.

[25] Jin B, van Leeuwen J (Hans), Yu Q, Patel B. Screening and selection of microfungi for microbial biomass protein production and water reclamation from starch processing wastewater. J Chem Technol Biotechnol 1999; 74:106-10.

[26] Jin B, Yan X Q, Yu Q, van Leeuwen J (Hans). A comprehensive pilot plant system for fungal biomass protein production from starch wastewater. Adv Environ Res 2002; 6:179-89.

[27] Jin B, Yu Q, van Leeuwen J (Hans). A bioprocessing mode for fungal biomass protein production and wastewater treatment using an external airlift bioreactor. J Chem Technol Biotechnol 2001; 76:1041-48.

[28] Jin B, Yu Q, van Leeuwen J (Hans), Hung Y T. Integrated biotechnological fungal biomass protein production and wastewater reclamation, environmental bioengineering. In: Wang L K, Tay J H, Tay S T L, Hung Y T, editors. Handbook of environmental engineering, volume 11, Totowa, N.J., USA: The Humana Press, Inc.; 2009, p. 465.

[29] Jin B, Yu Q, Yan X Q, van Leeuwen J (Hans). Characterization and improvement of oxygen transfer in pilot plant external air-lift bioreactor for mycelial biomass production and wastewater treatment. World J Appl Microbiol Biotechnol 2001b; 17:265-72.

[30] Rasmussen M, Kambam Y, Khanal S K, Pometto III A L, van Leeuwen J (Hans). Thin stillage treatment from dry-grind ethanol plants with fungi. Minneapolis, Minn., USA: American Society of Agricultural and Biological Engineers (ASABE) Annual International Meeting; 2007.

[31] Sankaran S, Khanal S K, Pometto III A L, van Leeuwen J (Hans). Ozone as a selective disinfectant for nonaseptic fungal cultivation on corn-processing wastewater. Bioresour Technol 2008; 99(17):8265-73.

[32] Nigam P. Process selection for protein-enrichment: fermentation of the sugar industry byproducts molasses and sugar beet pulp. Process Biochem 1994; 29(5):337-42.

[33] American Public Health Association/American Water Works Association/Water Environment Federation (APHA/AWWA/WEF). Standard methods for the examination of water and wastewater. 21st ed. Washington D.C., USA: APHA/AWWA/WEF; 2005.

[34] Association of Official Analytical Chemists (AOAC). Official methods of analysis. 17th ed. Virginia, USA: AOAC International; 2005.

[35] Antai S P, Crawford D L. Degradation of softwood, hardwood, and grass lignocelluloses by two *Streptomyces* strains. Appl Environ Microbiol 1981; 42:378-80.

[36] Dubois M, Gilles K A, Hamilton J K, Rebers P A, Smith F. Colorimetric method for determination of sugars and related substances. Anal Chem 1956; 28(3):350-56.

[37] Kunduru M R, Pometto III A L. Continuous ethanol production by *Zymomonas mobilis* and *Saccharomyces cerevisiae* in biofilm bioreactors. J Ind Microbiol 1996; 16:249-56.

[38] Walker G M. Yeast physiology and biotechnology. Chichester, UK: John Wiley & Sons; 1998.

[39] Zhang Z Y, Jin B, Kelly J M. Production of lactic acid from renewable materials by *Rhizopus* fungi. Biochem Eng J 2007; 35:251-63.

[40] Sparring a R A, Owens J D. Causes of alkalinization in tempe solid substrate fermentation. Enzyme Microb Technol 1999; 25:677-81.

[41] Cheeke P R. Applied animal nutrition: Feeds and feed. New Jersey, USA: Pearson Education, Inc.; 2005.

[42] National Research Center (NRC). Nutrient requirements of swine. 10th Ed. Washington D.C.: National Academies Press; 1998.

The process described herein provides various advantages over current mechanisms and production facilities. The process of the present invention to provide a means of generating revenue from low-value stillage, and other crop processing liquid left-overs, while reducing the purification costs of this stream. The process also establishes a simple treatment technology with easy recovery of additional co-products generated. The process further cultivates beneficial fungi at ethanol plants using stillage as a substrate. In addition, the process of the present invention provides a means of averting the energy requirements and costs associated with thin stillage evaporation during ethanol production. It provides a mechanism by which to lower the solids and dissolved organic concentrations during treatment of stillage to enable direct reuse of the water in yeast fermentation earlier in the ethanol process.

The process described herein provides various unexpected results and advantages. It was not obvious before doing the research leading up to the invention that the molds would be able to utilize the organic substances in thin stillage, soy and other plant seed processing leftovers, or if they would be inhibited in their growth by some of the constituents in thin stillage or other co-products in liquid leftovers. It is a significant that a variety of filamentous fungi can be cultivated readily on stillage as the atmosphere is under traditional understanding not favorable to cultivation. In fact, contrary to traditional understanding, the inhibitory substances in stillage are removed and utilized by the filamentous. The high organic content, and ratio of COD to nitrogen and phosphorus level is favorable, but the high level of lactic and acetic acids and glycerol is under traditional understanding likely to inhibit fungal growth as these substances are inhibitory to yeasts, which are also fungi. To the contrary, all of these inhibitory substances are removed and utilized by the filamentous fungi.

Additionally, easy separation and dewatering is important in the economical operation. Moreover, unlike traditional processes, the fungal process described herein provides for direct water recycling, saving considerable expense in evaporation, condensation and further treatment. Enmeshment of the solid particles in thin stillage by the fungal mycelia leads to 99% or more removal of suspended solids. This makes for very clear water, important for recycling in order not to build up the inert solids in the yeast fermentation process and also recovers this part of material as animal feed. The ability to recycle water directly after fungal treatment leads to savings in the use of sulfuric acid commonly used to adjust the pH of the yeast fermentation process. The water is maintained at a low pH during fungal fermentation, thereby preserving the acidity for reuse. A further unexpected outcome is a beneficial effect on the distillers grains as less sulfuric acid use will reduce undesirable sulfate. Enzymes are also retained and preserved in the water and can be recycled with the water without further treatment that could denature the enzymes, saving significant cost over traditional processes.

The process described herein is very economical compared with the current practice of evaporating most of the water in the stillage. The present invention eliminates the need for evaporation by removing the dissolved organic material through a fungal cultivation process. The energy savings from eliminating thin stillage evaporation could amount to $250 million/year nationwide at 2008 ethanol production levels. Excess enzymes recycled with fungal-treated water from thin stillage could also add value of millions of dollars per year. The potential revenue from value-added animal feed production along with expanding the market value of DDG is expected to be worth another $200-$400 million/year.

Moreover, under the fungal process disclosed herein, it is not necessary to autoclave the stillage to avoid bacterial competition in fermentation. The fungal biomass can be easily separated and dewatered by screening, settling or floatation, providing economic benefits through lower cost to operation.

As described above, the process permits a shorter SRT than HRT, as compared to what would normally be a challenge in a bioreactor operation, but since the fungal pellets are so easily harvested, continuous harvesting from a side-stream pumped through a screen makes for easy continuous operation. Oil collection in the fungal process contributes to making the process more economical by generating a valuable co-product. Oil separation in the fungal process contributes to making the ethanol production process more economical by generating a value of about 2 c/gallon ethanol produced. Using oleaginous fungi to produce further oil as myco-oil is another advantageous approach to enhance the profitability of seed processing co-product beneficiation. The fungal biomass is further a viable food source with an acceptable taste and no known after-effects.

In addition to the foregoing, the fungal biomass is an ideal source of the nutraceuticals chitin, chitosan and glucosamine, constituting 5-9% of the biomass, traditionally obtained from crustaceans. The current wholesale value of these substances is over $8,000 per ton. Chitin and its derivatives: chitosan and chitosan oligosaccharides have unique characteristics, which have several health benefits to swine and probably poultry as a prebiotic and immunity enhancer. Chitosan oligosaccharides (COS) improve animal health and eliminate the use of antibiotics in feed. The major source of chitin-derived chitosan oligosaccharides (COS) has been crustacean exoskeletons. The supply from such sources, particularly in the United States, is limited due to logistics of collection and also because the extraction process is highly polluting. The fungal production on thin stillage provides a new opportunity to produce such compounds right in the heart of biofuel and livestock production regions with a non-polluting process.

In addition, the waste organic matter is used as a substrate for growth of biomass that can be sold in the U.S. animal feed markets, and more importantly, to a large potential market for feeding monogastric animals. There is a growing demand all over the world for protein, which can be used as an animal feed supplement or in pet food. Protein shortages are a major cause of famine and human malnutrition related diseases such as kwashiorkor. Ultimately, there is a demand for high quality protein for human consumption. The product, is edible, not bad-tasting and an unexpected food source. Furthermore, the fungal biomass can serve as a source of valuable nutraceuticals, such as chitin, chitosan and glucosamine.

Persons skilled in the art will readily appreciate that the processes described above may in some instances be combined or separated into several steps. Furthermore, persons skilled in the art will also readily appreciate that the processes of this invention may be accomplished using a variety of equipment and techniques that are well known in the art. The specific equipment and processes used are not crucial so long as the intended result is accomplished.

It should be appreciated that minor modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method for cultivating fungi, the method comprising: cultivation of filamentous fungi of the phyla Zygomycota and Ascomycota, excluding the order Saccharomycetales, in a fungal bioreactor with stillage left over after distillation of alcohols from a fermented mash of plant material;
said stillage is a substrate for said filamentous fungi;
said filamentous fungi forming a fungal biomass; and
harvesting said fungal biomass.

2. The method of claim 1 wherein the stillage used is from a dry-grind corn milling ethanol plant.

3. The method of claim 1 wherein the plant material is soy processing whey.

4. The method of claim 1 wherein the fungi are selected from the group of filamentous fungi consisting of the genera *Aspergillus, Fusarium, Rhizopus, Mucor, Rhizomucor, Absidia, Backusella, Penicilium* and mixtures of the same.

5. The method of claim 1 wherein the fungal genera are selected from the family Mucoraceae.

6. The method of claim 5, wherein the fungal genera are selected from the group consisting of *Rhizopus microsporus* and *Mucor indicus*.

7. The method of claim 5 wherein the fungal genera are selected from the group consisting of *Absidia, Backusella, Rhizopus, Mucor, Rhizomucor*, and mixtures thereof.

8. The method of claim 1 wherein substantially all suspended solids are removed from thin stillage and said resulting thin stillage is purified by fungi in a fungal bioreactor by removal of dissolved organic substances.

9. The method of claim 1 further comprising removal of acetic acid present in the stillage by the fungal culture.

10. The method of claim 1 further comprising removal of lactic acid present in the stillage by the fungal culture.

11. The method of claim 1 further comprising removal of glycerol present in the stillage by the fungal culture.

12. The method of claim 1 further comprising removal of suspended and dissolved organic compounds from stillage by enmeshment by the fungal culture.

13. The method of claim 1 further comprising dewatering and drying the fungal biomass with enmeshed solids for use as animal feed.

14. The method of claim 1 further comprising dewatering and drying the fungal biomass for the manufacture of food for consumption.

15. The methods of claim 1 further comprising drying the fungal biomass as a source of or raw material for extracting nutraceuticals.

16. The method of claim 1, wherein water is recovered and directly recycled to a fermentation process.

17. The method of claim 16 wherein enzymes are recovered with the water and recycled to the fermentation process.

18. The method of claim 16 wherein pH is maintained by the direct recycling of water.

19. The method of claim 18 whereby acid used for pH control is recovered with the water for recycling to the fermentation process.

20. The method of claim 1, wherein enzymes are produced by the fungi.

21. The method of claim 1 wherein the bioreactor is an airlift reactor for the fungal cultivation, the airlift reactor enhancing the fungal morphology to grow into pellets.

22. The method of claim 1, further comprising cultivating said filamentous fungi in aerobic conditions.

23. The method of claim 1, further comprising recovering water.

24. The method of claim 1 wherein fungal pellets are formed by the cultivation step, and wherein the method further comprises harvesting and dewatering the fungal pellets with course screens of openings ranging from 1 mm to 8 mm.

25. The method of claim 1 wherein fungal pellets are formed by the cultivation step, and wherein the method further comprises separating and harvesting the fungal pellets from a resulting liquid by settling and/or flotation.

26. The method of claim 1 wherein fungal pellets are formed by the cultivation step, and wherein the method further comprises dewatering the harvested fungal biomass using any one of a filter press, a belt press, and a centrifuge.

27. The method of claim 1, further comprising releasing corn oil in the stillage through fungal action on at least one of suspended solids and breaking oil emulsions.

28. The method of claim 27, further comprising recovering oil from stillage by at least one of enmeshment and adsorption in fungal biomass.

29. The method of claim 27, further comprising separating and recovering plant oil in stillage by flotation and skimming.

30. The method of claim 27, further comprising releasing oil in the stillage through fungal action on at least one of suspended solids and breaking oil emulsions when applied to the stillage left over from ethanol production from corn and collecting this oil by adsorption on the fungal biomass.

31. The method of claim 1 further comprising cultivating oleaginous fungi as found among the Zygomycota, to produce oil by the conversion of carbohydrates into oil inside the fungal cells.

32. The method of claim 31 further comprising cultivating *Mucor circinelloides*, to produce oil by the conversion of carbohydrates into oil inside the fungal cells.

33. The method of claim 31 further comprising producing oil that can be withdrawn by dewatering, drying and some form of extraction by the use of a solvent.

34. A method for cultivating fungi, the method comprising cultivation of fungi of the phyla and Zygomycota and Ascomycota, excluding the order Saccharomycetales, in a fungal bioreactor with, as a substrate, water containing organic leftovers resulting from a process of distillation of alcohols from a fermented mash of plant material;
said cultivation occurring in aerobic conditions;
said fungi creating a fungal biomass;
harvesting said fungal biomass; and
recovering water.

35. A method consisting essentially of treating stillage left over after distillation of alcohols from a fermented mash of plant materials with filamentous fungi selected from the phyla consisting of Zygomycota, Ascomycota excluding the order Saccharomycetales, and combinations thereof, in a fungal bioreactor to grow fungal biomass.

* * * * *